(12) United States Patent
Frater et al.

(10) Patent No.: US 11,420,926 B2
(45) Date of Patent: Aug. 23, 2022

(54) METHODS OF MAKING OLEFINIC E- AND Z-ISOMERS

(71) Applicant: Verbio Vereinigte BioEnergie AG, Zorbig (DE)

(72) Inventors: Georg Frater, Horw/Lucerne (CH); Agota Bucsai, Budapest (HU); Krisztian Lorincz, Budapest (HU)

(73) Assignee: Verbio Vereinigte BioEnergie AG, Zorbig (DE)

( * ) Notice: Subject to any disclaimer, the term of this patent is extended or adjusted under 35 U.S.C. 154(b) by 41 days.

(21) Appl. No.: 16/617,428

(22) PCT Filed: May 30, 2018

(86) PCT No.: PCT/EP2018/064307
§ 371 (c)(1),
(2) Date: Nov. 26, 2019

(87) PCT Pub. No.: WO2018/220088
PCT Pub. Date: Dec. 6, 2018

(65) Prior Publication Data
US 2021/0122697 A1   Apr. 29, 2021

(30) Foreign Application Priority Data
May 30, 2017   (EP) ................................... 17173536

(51) Int. Cl.
| C07C 67/333 | (2006.01) |
| B01J 31/22 | (2006.01) |
| C07C 67/317 | (2006.01) |
| C07C 67/327 | (2006.01) |
| C07D 301/14 | (2006.01) |

(52) U.S. Cl.
CPC ......... C07C 67/333 (2013.01); B01J 31/2217 (2013.01); C07C 67/317 (2013.01); C07C 67/327 (2013.01); C07D 301/14 (2013.01); *B01J 2231/543* (2013.01); *C07B 2200/09* (2013.01)

(58) Field of Classification Search
CPC ..... C07C 67/317; C07C 67/31; C07C 67/327; C07C 67/343; C07C 67/333; C07C 69/593; C07C 69/675
See application file for complete search history.

(56) References Cited

FOREIGN PATENT DOCUMENTS

| WO | 2011040963 | 4/2011 |
| WO | 2013070725 | 5/2013 |
| WO | 2014172534 | 10/2014 |
| WO | 2014201300 | 12/2014 |

OTHER PUBLICATIONS

Back, et al., Effect of Chain Length and Ring Size of Alkyl and Cycloalkyl Side-Chain Substituents upon the Biological Activity fo Brassinosteriods. Preparation of Novel Analogues with Activity Excedding that of Brassinolide, J. Org. Chem, 65, 2000, 3047-3052.
Bakthavachalan, et al., A C2-Symmetric Chiral Pool-Based Flexible Strategy: Synthesis of (+)- and (−)-Shikimic Acids, (+)- and (−)-4-epi-Shikimic Acids, and (+)- and (−)-Pinitol, The Journal of Organic Chemistry, 79, 2014, 2898-2905.
Discordia, et al., Telluride-Mediated Stereospecific Conversion of Racemic E-Allylic Alcohols to Homochiral Z-Allylic Alcohols; Transposition of Primary and Secondary Allylic Alcohols VIA Glycidol Derivatives, Tetrahedron Letters, vol. 31 No. 39, 1990, 5603-5606.
Findlay, et al., Reductions of Challenging Organic Substrates by a Nickel Complex of a Noninnocent Crown Cardene Ligand, JACS Communications, 132, 2010, 15462-15464.
Schmidt, et al., A Synthesis of Densely Functionalized 2,3-Dihydropyrans Using Ring-Closing Metathesis and Base-Inducted Rearrangements of Dihydropyran Oxides, Euro. J. Org Chem., 2000, 3145-3163.
Yu, et al., Regioselective and Stereospecific Copper-Catalyzed Deoxyenation of Epoxides to Alkenes, ACS Publications, Organic Letters, 18, 2016, 4734-4737.

*Primary Examiner* — Ana Z Muresan
(74) *Attorney, Agent, or Firm* — Dorsey & Whitney LLP

(57) ABSTRACT

Method of making a second olefin using a first olefin, comprising steps (A) and (B): (A) performing a metathesis reaction with the first olefin in the presence of a metal complex configured to catalyse said metathesis reaction; (B) epoxidizing an olefin contained in the reaction mixture obtained in step (A) to form an epoxide; and deoxygenizing said epoxide to form said second olefin.

15 Claims, No Drawings

METHODS OF MAKING OLEFINIC E- AND Z-ISOMERS

RELATED APPLICATIONS

This application is a National Stage Entry of International Application No. PCT/EP2018/064307, filed May 30, 2018, which claims priority to European Patent Application No. 17173536.8, filed May 30, 2017, each of which is incorporated herein by reference in its entirety.

FIELD OF THE INVENTION

The invention relates to a method of making an olefin, the method combining a metathesis reaction with the reaction of transforming an E-olefin to a Z-olefin, or vice versa.

BACKGROUND OF THE INVENTION

Reactions of forming e.g. an acyclic olefin may result in a mixture of the E-isomer (trans) as the thermodynamically controlled product and the Z-isomer (cis) as the kinetically controlled product. Depending on the activation energy required for the reaction, the E-isomer and Z-isomer may be present in various amounts. E.g., in olefin metathesis, using non-selective catalysts, mixtures of E- and Z-isomers may be obtained, in which the E-isomer predominates. Typically, such mixtures contain the E- and Z-isomers in a ratio around 80:20. However, a variety of chemical processes requires that for the further processing the individual isomers are provided in a rather pure stereoisomeric form. Due to similar physical properties such as the boiling point, the E- and Z-isomer are normally not easy to separate from one another e.g. by distillation which is the method of choice at an industrial scale.

Moreover, in case the Z-isomer is needed for further processing, it is not beneficially in view of an industrial application to isolate the Z-isomer from mixtures in which the E-isomer predominates and to sacrifice the E-isomer, and vice versa.

It is further known in olefin metathesis to promote the formation of the Z-isomer compared to the E-isomer, e.g. in a molar ratio of more than 95:5, by using appropriate Z-selective metal complexes as catalysts. Suitable Z-selective catalysts for promoting the formation of Z-isomers over the formation of E-isomers are e.g. Z-selective aryloxy pyrrolide complexes of molybdenum and tungsten or Z-selective ruthenium catalysts as disclosed e.g. in WO 2014/201300, WO 2011/040963, WO 2014/172534 and WO 2013/070725.

Contrary to this, it is however difficult to promote a metathesis reaction such that the E-isomer is formed in a molar ratio compared to the Z-isomer of more than 95 to 5 (Shen, X. et al., "Kinetically E-selective macrocyclic ring-closing metathesis", Nature 541, pages 380-385; doi: 10.1038/nature20800). However, highly pure E-isomers are important for synthetic chemistry.

OBJECTS OF THE INVENTION

It was the object of the invention to provide a method for obtaining olefinic Z-isomers from mixtures containing the respective E- and Z-isomers, preferably in which the E-isomer predominates, and obtaining E-isomers from mixtures containing the respective E- and Z-isomers, preferably in which the Z-isomer predominates. The respective isomers should be obtained in a high yield and stereoisomeric purity.

SUMMARY OF THE INVENTION

This object was achieved with a method of combining a metathesis reaction with a method of transforming an E-isomer of an olefin into the Z-isomer, and with a method of combining a metathesis reaction with a method of transforming a Z-isomer into an E-isomer.

More specifically, according to a first aspect of the invention, the combination of the two reactions allows the enrichment of an E-isomer being present in an olefin comprising the E-isomer and the Z-isomer, preferably wherein said E-isomer predominates the Z-isomer. The method requires that in a first step the Z-isomer is removed or degraded in a kinetically controlled metathesis reaction such that the E-isomer substantially is not reacted. Accordingly, the E-isomer is enriched. In a second step, the thus enriched E-isomer is converted to the Z-isomer. In sum, the Z-isomer is obtained in a high stereoisomeric purity and yield.

According to a second aspect of the invention, the combination of the two reactions allows in a first step to make an olefinic Z-isomer in a metathesis reaction in a high stereoisomeric purity and yield compared to the E-isomer while using Z-selective metal complexes as catalysts. In a second step, the thus made Z-isomer is converted to the E-isomer. In sum, the E-isomer is obtained in a high stereoisomeric purity and yield.

This makes the combination of the reactions according to the invention extraordinarily valuable in olefin chemistry.

The invention relates to a method as defined in item 1:
1. Method of making a second olefin using a first olefin, comprising steps (A) and (B):
   (A) performing a metathesis reaction with the first olefin in the presence of a metal complex configured to catalyse said metathesis reaction in order to obtain a reaction mixture containing an olefin;
   (B) epoxidizing the olefin contained in the reaction mixture obtained in step (A) to form an epoxide; and deoxygenizing said epoxide to form said second olefin.

The invention further relates to the following embodiments which are numbered hereinunder under the following items 2 to 17:

2. Method of item 1, wherein the first olefin comprises an E-isomer and a Z-isomer of the first olefin.
3. Method of item 1 or 2, wherein the ratio of the E-isomer to the Z-isomer is in the range of from 1:1 to 9:1, preferably in the range of from 2:1 to 9:1.
4. Method of item 2 or 3, wherein said second olefin is said Z-isomer, further comprising the enrichment of the E-isomer over the Z-isomer, and the subsequent conversion of the E-isomer into the Z-isomer to form the second olefin, wherein step (A) comprises step (A1):
   (A1) subjecting the first olefin comprising a mixture of the E-isomer and the Z-isomer to a cross metathesis reaction with a third olefin in the presence of a metal complex configured to favour the reaction of said third olefin with said Z-isomer over the reaction of said third olefin with said E-isomer.
5. Method of item 4, wherein said third olefin is a $C_{2-10}$ olefin, preferably a terminal $C_{2-10}$ olefin.
6. Method of item 4 or 5, wherein said third olefin is ethylene.

7. Method of any one of items 4 to 6, further comprising step (A2):
   (A2) separating off the E-isomer enriched in step (A1).
8. Method of any one of items 4 to 7, further comprising converting the E-isomer enriched in step (A1) or separated off in step (A2) to the Z-isomer, the conversion comprising steps (B1) to (B4):
   (B1) epoxidizing said E-isomer;
   (B2) subjecting the epoxide obtained in step (B1) to hydrolysis or alcoholysis;
   (B3) converting the diol or beta-hydroxy ether obtained in step (B2) to a 1,3-dioxolane;
   (B4) degrading the 1,3-dioxolane obtained in step (B3) to form the second olefin in the form of its Z-isomer.
9. Method of item 8, wherein step (B3) comprises the reaction of the diol obtained in step (B2) with thiophosgen or 1,1'-thiocarbonyldiimidazol; and step (B4) comprises the reaction with a trialkylphosphite.
10. Method of item 8, wherein step (B3) comprises the reaction of the diol or beta-hydroxy ether obtained in step (B2) with an ortho carboxylic acid ester; and step (B4) comprises the pyrolysis of the formed 1,3-dioxolane.
11. Method of any one of the preceding items, wherein the first olefin used in step (A) or step (A1) is or comprises a mixture of an E- and a Z-9-dodecenoate, preferably the methyl ester, the olefin contained in the reaction mixture obtained in step (A) or enriched in step (A1) is the E-9-dodecenoate, and the second olefin obtained after step (B) or steps (B1) to (B4) is the Z-9-dodecenoate, preferably in a stereoisomeric purity of more than 95%.
12. Method of item 1 or 2, wherein the ratio of the Z-isomer to the E-isomer is at least 9:1.
13. Method of item 12, wherein said second olefin is said E-isomer, and step (A) comprises step (A11):
    (A11) subjecting the first olefin to a cross metathesis reaction with a fourth olefin in the presence of a metal complex to form a fifth olefin, wherein the metal complex is configured to favour the formation of the Z-isomer over the formation of the E-isomer of the fifth olefin.
14. Method of item 13, further comprising the subsequent conversion of the Z-isomer into the E-isomer to form the second isomer, wherein step (B) comprises steps (B11) to (B14):
    (B11) epoxidizing said Z-isomer;
    (B12) subjecting the epoxide obtained in step (B11) to hydrolysis to form a diol or to alcoholysis to form a beta-hydroxy ether;
    (B13) converting the diol or beta-hydroxy ether obtained in step (B12) to a 1,3-dioxolane;
    (B14) degrading the 1,3-dioxolane obtained in step (B13) to form the second olefin in the form of its E-isomer.
15. Method of any one of items 12 to 14, wherein the first and the fourth olefin are identical and are a 9-decenoate, preferably methyl 9-decenoate.
16. Method of any one of items 4 to 15, wherein the metal complex is selected from a compound of formula (I):

$$\begin{array}{c} R^4 \underset{R^3}{\overset{X}{\underset{\|}{\overset{\|}{M}}}} \underset{(R^z)_n}{\overset{R^1}{\underset{}{}}} R^2 \end{array} \qquad (I)$$

wherein
M=Mo or W
X=O or N—$R^5$;
$R^1$=H;
$R^2$=CMe$_3$; CMe$_2$Ph; or o-C$_{1-6}$-alkoxyphenyl, optionally substituted;
$R^3$=substituted aryloxy, preferably substituted phenyloxy, substituted naphthyl-2-oxy or substituted 5,6,7,8-tetrahydronaphthyl-2-oxy, or substituted naphthyl-1-oxy;
$R^4$=pyrrol-1-yl, 2,5-dimethylpyrrol-1-yl; or 2,5-diphenylpyrrol-1-yl; or substituted or unsubstituted indol-1-yl;
$R^5$=C$_{6-20}$ aryl or C$_{4-10}$ alkyl; optionally substituted.
$R^z$=neutral ligand;
n=0 or 1;
or
from a compound of formula (II):

$$\begin{array}{c} (R^1)_r \\ R^{14}=\underset{L}{\overset{|}{\underset{|}{M}}} \overset{R^4}{\underset{R^5}{\diagdown}} \end{array} \qquad (II)$$

wherein
M=Ru;
each of $R^1$ and L is a neutral ligand;
r=1-3
each of $R^4$ and $R^5$ is independently bonded to M through sulfur or oxygen; or $R^4$ and $R^5$ are halogen, preferably Cl;
$R^{14}$ is a carbene;
or
from a compound of formula (III):

$$\begin{array}{c} R^3-N \overset{Q}{\diagup} \overset{}{\diagdown} N-R^4 \\ \underset{X^1}{\diagdown} \overset{Q^*}{\underset{Ru}{\diagup}} \overset{}{\diagdown} \overset{R^8}{\diagup} \\ \underset{Z}{\diagdown} O \overset{}{\diagdown} \overset{R^7}{\diagup} \\ R^5 \quad R^6 \end{array} \qquad (III)$$

wherein
Q is a hydrocarbylene, or alkyl-substituted hydrocarbylene;
Q* forms a carbon-ruthenium bond with the carbon from the $R^3$ group;
X' is nitrate, or C$_{1-20}$ alkylcarboxylate;
$R^3$ is cycloalkyl or an alkyl substituted cycloalkyl group;
$R^4$ is an alkyl substituted aryl group;
Z is alkyl; and
$R^5$, $R^6$, $R^7$ and $R^8$ are hydrogen.

17. Method of item 16, wherein the catalyst is selected from
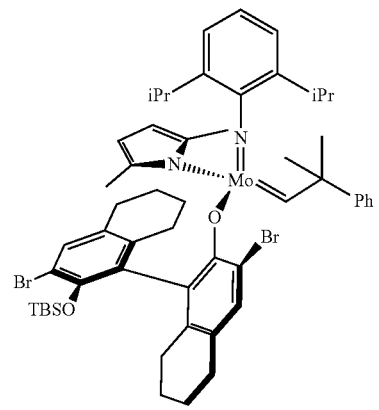
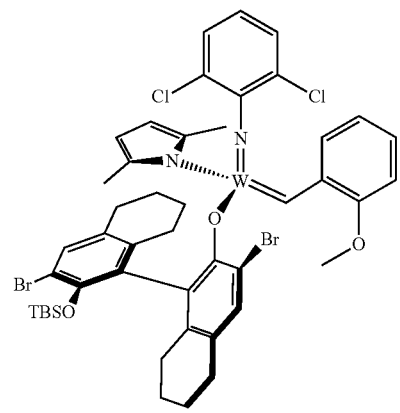
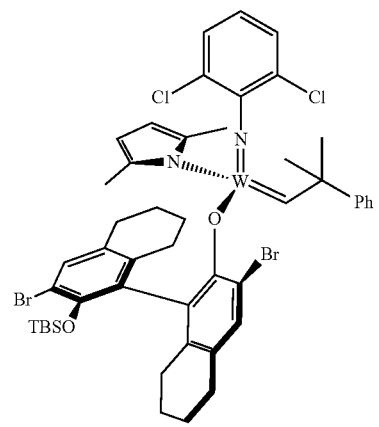
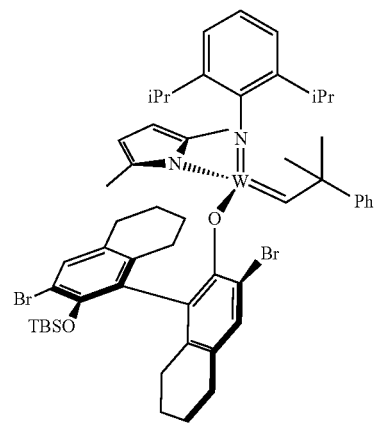
-continued
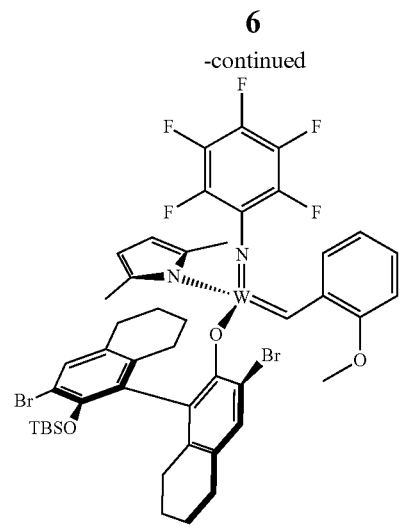
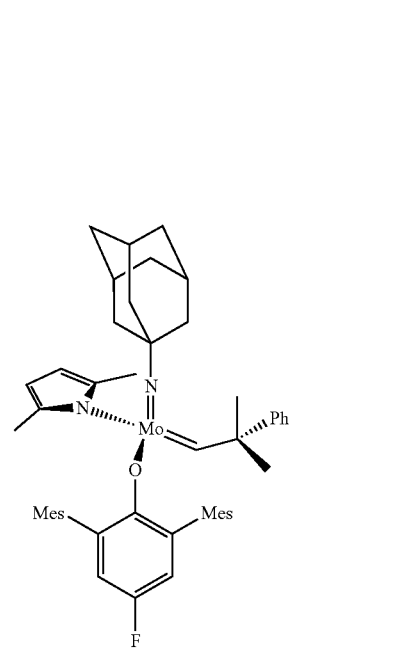
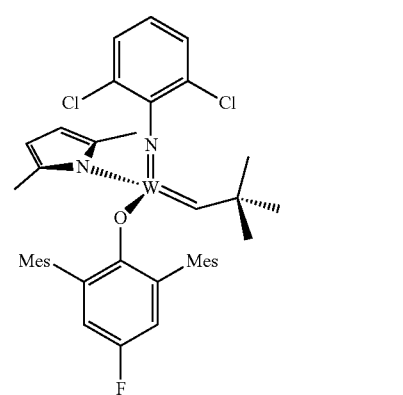

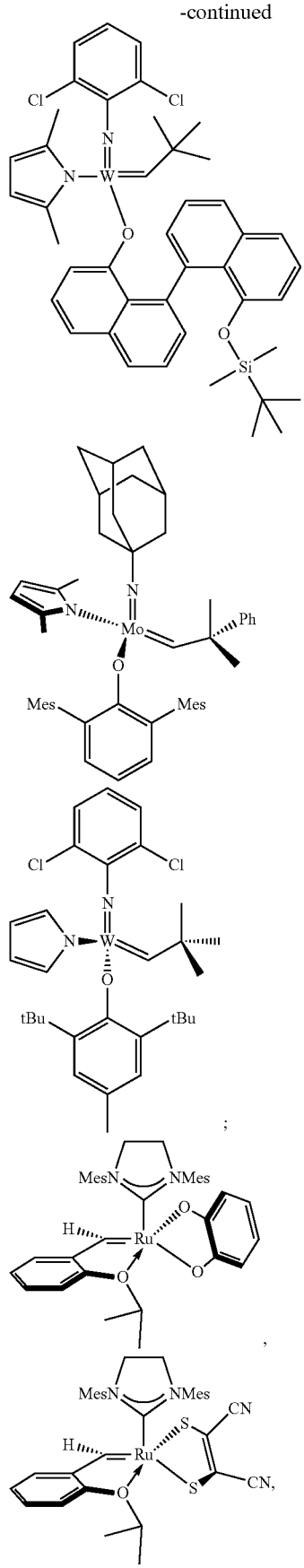

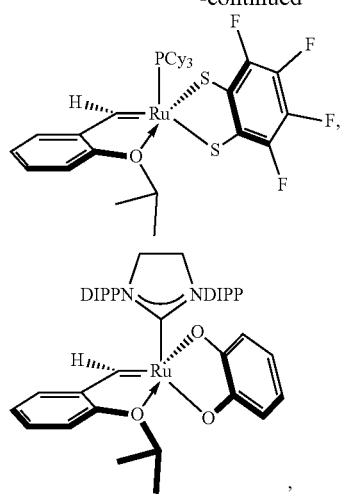
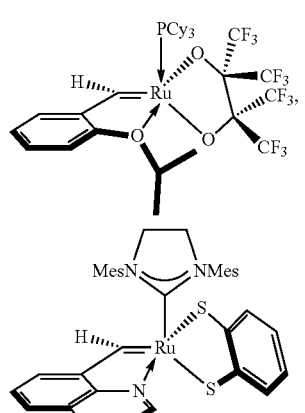
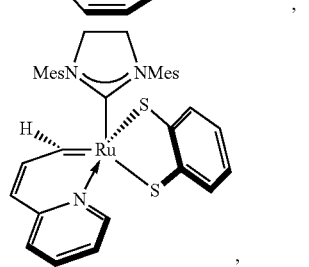
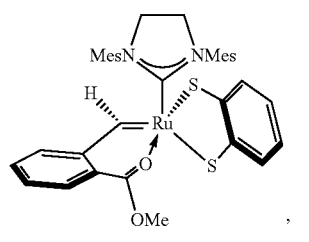
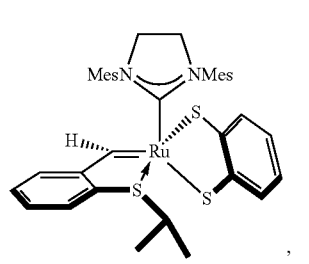
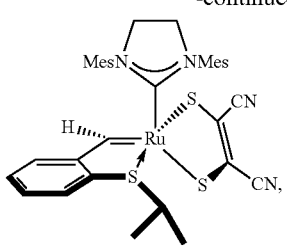
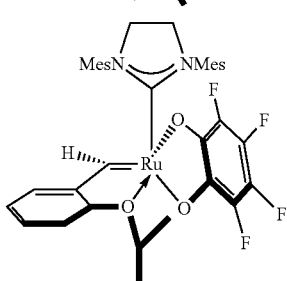
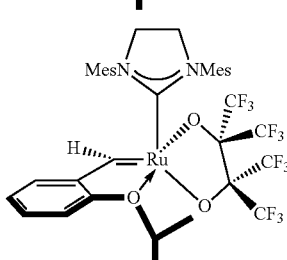
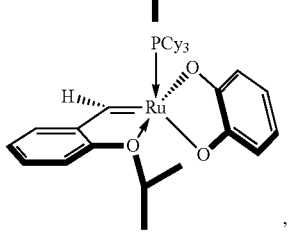
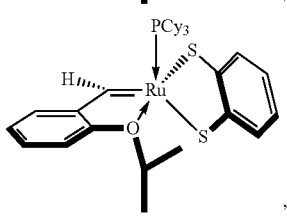
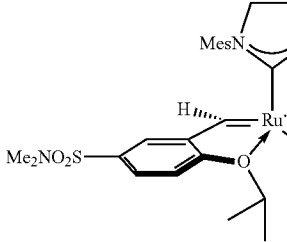
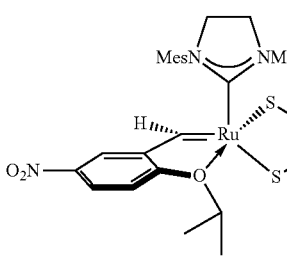
, and

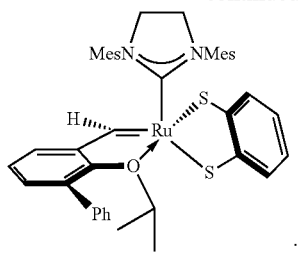
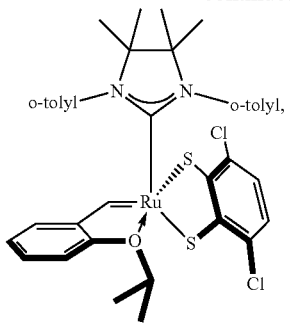
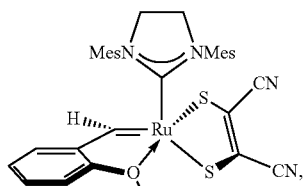
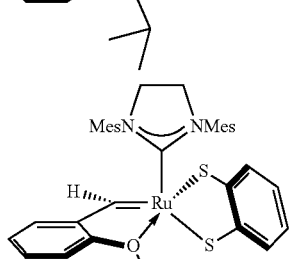
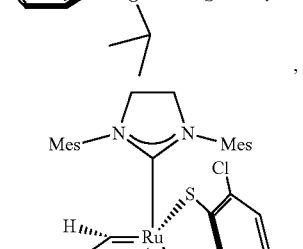
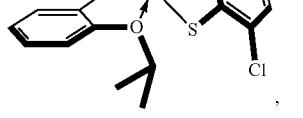

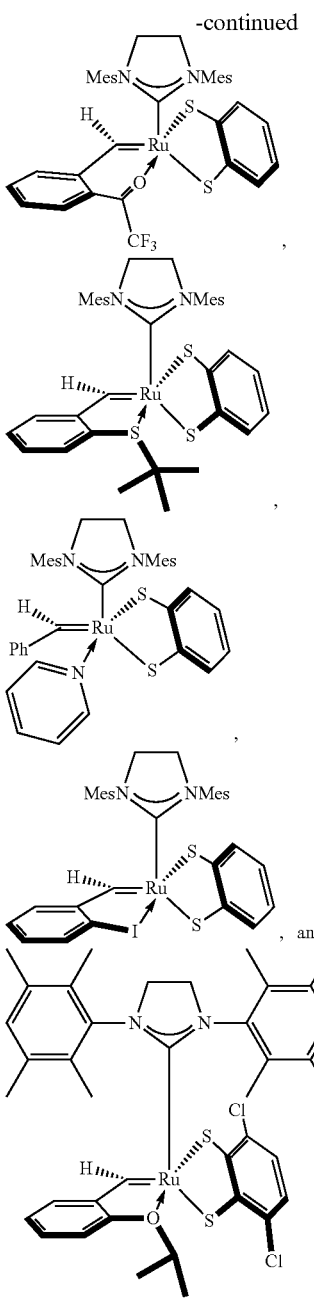

(Mes=mesityl; Cy=cyclohexyl; DIPP=diisopropyphenyl; TBS=tert.-butyldimethylsilyl; mes=mesitylene; Ad=1-adamantyl; Ph=phenyl; TMS=trimethylsilyl; Me=methyl; pr=propyl).

The invention encompasses in particular aspects the following items:

1. Method of making a second olefin using a first olefin, comprising steps (A) and (B):
   (A) performing a metathesis reaction with the first olefin in the presence of a metal complex configured to catalyse said metathesis reaction in order to obtain a reaction mixture containing an olefin;
   (B) epoxidizing the olefin contained in the reaction mixture obtained in step (A) to form an epoxide; and deoxygenizing said epoxide to form said second olefin;
   wherein the first olefin comprises an E-isomer and a Z-isomer of the olefin;
   wherein the ratio of the E-isomer to the Z-isomer is in the range of from 1:1 to 9:1 wherein said second olefin is said Z-isomer, further comprising the enrichment of the E-isomer over the Z-isomer, and the subsequent conversion of the E-isomer into the Z-isomer to form the second olefin, wherein step (A) comprises step (A1):
   (A1) subjecting the first olefin comprising a mixture of the E-isomer and the Z-isomer to a cross metathesis reaction with a third olefin in the presence of a metal complex configured to favour the reaction of said third olefin with said Z-isomer over the reaction of said third olefin with said E-isomer;
   and further comprising converting the E-isomer enriched in step (A1) to the Z-isomer, the conversion comprising steps (B1) to (B4):
   (B1) epoxidizing said E-isomer;
   (B2) subjecting the epoxide obtained in step (B1) to hydrolysis or alcoholysis;
   (B3) converting the diol or beta-hydroxy ether obtained in step (B2) to a 1,3-dioxolane;
   (B4) degrading the 1,3-dioxolane obtained in step (B3) to form the second olefin in the form of its Z-isomer.

2. Method of item 1, wherein the ratio of the E-isomer to the Z-isomer is in the range of from 2:1 to 9:1.

3. Method of item 1 or 2, wherein said third olefin is a $C_{2-10}$ olefin, preferably a terminal $C_{2-10}$ olefin.

4. Method of any one of the preceding items 1 to 3, wherein said third olefin is ethylene.

5. Method of any one of the preceding items 1 to 4, wherein step (B3) comprises the reaction of the diol obtained in step (B2) with thiophosgen or 1,1'-thiocarbonyldiimidazol; and step (B4) comprises the reaction with a trialkylphosphite; or
   wherein step (B3) comprises the reaction of the diol or beta-hydroxy ether obtained in step (B2) with an ortho ester; and step (B4) comprises the pyrolysis of the formed 1,3-dioxolane.

6. Method of any one of the preceding items 1 to 5, wherein the first olefin used in step (A) or step (A1) is or comprises a mixture of an E- and a Z-9-dodecenoate, preferably the methyl ester, the olefin contained in the reaction mixture obtained in step (A) or enriched in step (A1) is the E-9-dodecenoate, and the second olefin obtained after step (B) or steps (B1) to (B4) is the Z-9-dodecenoate, preferably in a stereoisomeric purity of more than 95%.

7. Method of making a second olefin using a first olefin, comprising steps (A) and (B):
   (A) performing a metathesis reaction with the first olefin in the presence of a metal complex configured to catalyse said metathesis reaction in order to obtain a reaction mixture containing an olefin;
   (B) epoxidizing the olefin contained in the reaction mixture obtained in step (A) to form an epoxide; and deoxygenizing said epoxide to form said second olefin;
   wherein the first olefin comprises an E-isomer and a Z-isomer of the olefin; and
   wherein the ratio of the Z-isomer to the E-isomer is at least 9:1; wherein said second olefin is said E-isomer, and step (A) comprises step (A11):
   (A11) subjecting the first olefin to a cross metathesis reaction with a fourth olefin in the presence of a metal complex to form a fifth olefin, wherein the metal complex is configured to favour the formation of the Z-isomer over the formation of the E-isomer of the fifth olefin;

and further comprising the subsequent conversion of the Z-isomer into the E-isomer to form the second olefin, wherein step (B) comprises steps (B11) to (B14):

(B11) epoxidizing said Z-isomer;

(B12) subjecting the epoxide obtained in step (B11) to hydrolysis to form a diol or to alcoholysis to form a beta-hydroxy ether;

(B13) converting the diol or beta-hydroxy ether obtained in step (B12) to a 1,3-dioxolane;

(B14) degrading the 1,3-dioxolane obtained in step (B13) to form the second olefin in the form of its E-isomer.

8. Method of any one of the preceding items, wherein the metal complex is selected from a compound of formula (I):

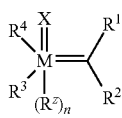

wherein

M=Mo or W

X=O or N—$R^5$;

$R^1$=H;

$R^2$=$CMe_3$; $CMe_2Ph$; or o-$C_{1-6}$-alkoxyphenyl, optionally substituted;

$R^3$=substituted aryloxy, preferably substituted phenyloxy, substituted naphthyl-2-oxy or substituted 5,6,7,8-tetrahydronaphthyl-2-oxy, or substituted naphthyl-1-oxy;

$R^4$=pyrrol-1-yl, 2,5-dimethylpyrrol-1-yl; or 2,5-diphenylpyrrol-1-yl; or substituted or unsubstituted indol-1-yl;

$R^5$=$C_{6-20}$ aryl or $C_{4-10}$ alkyl; optionally substituted.

$R^z$=neutral ligand;

n=0 or 1;

or from a compound of formula (II):

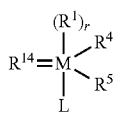

wherein

M=Ru;

each of $R^1$ and L is a neutral ligand;

r=1-3;

each of $R^4$ and $R^5$ is independently bonded to M through sulfur or oxygen; or $R^4$ and $R^5$ are halogen, preferably Cl;

$R^{14}$ is a carbene;

or from a compound of formula (III):

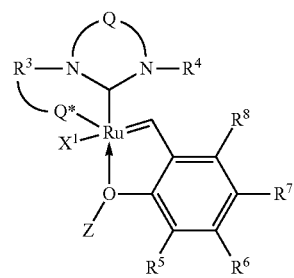

wherein

Q is a hydrocarbylene, or alkyl-substituted hydrocarbylene;

Q* forms a carbon-ruthenium bond with the carbon from the $R^3$ group;

$X^1$ is nitrate, or $C_{1-20}$ alkylcarboxylate;

$R^3$ is cycloalkyl or an alkyl substituted cycloalkyl group;

$R^4$ is an alkyl substituted aryl group;

Z is alkyl; and $R^5$, $R^6$, $R^7$ and $R^8$ are hydrogen.

9. Method of item 8, wherein the catalyst is selected from

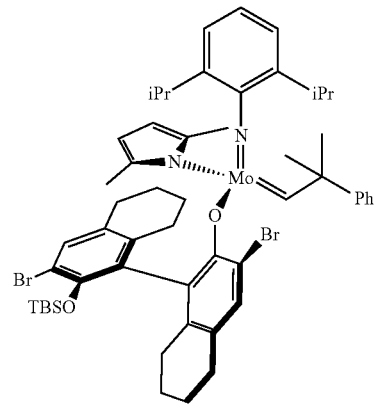

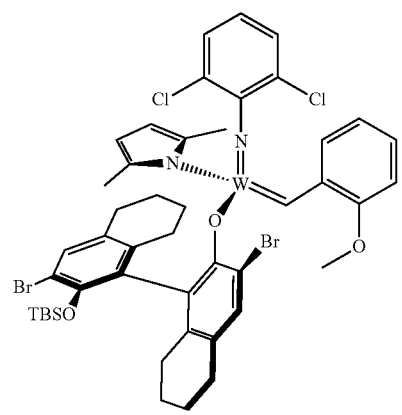

-continued
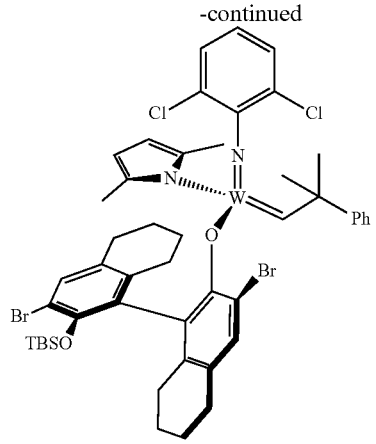
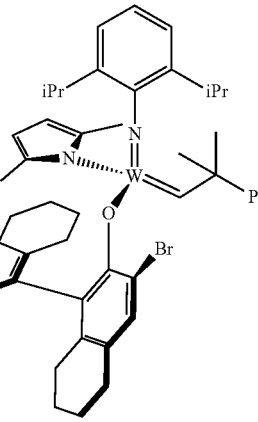
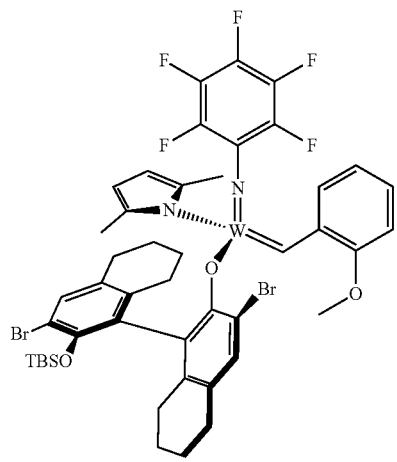
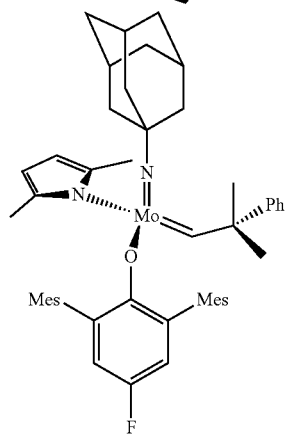
-continued
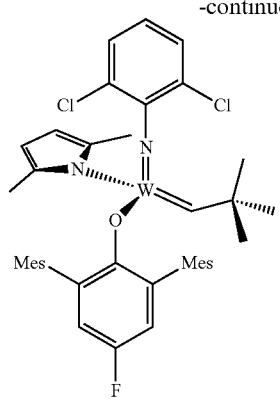
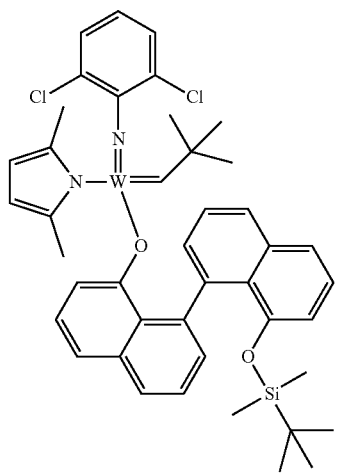
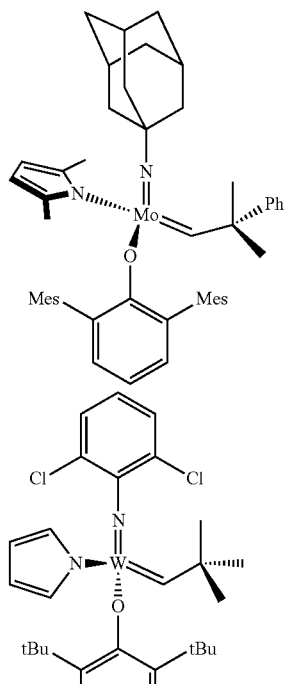

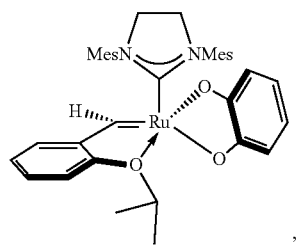
,
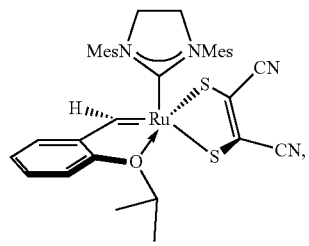
,
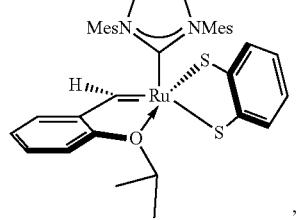
,
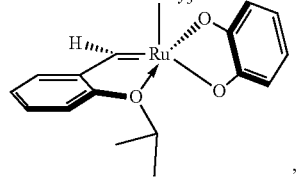
,
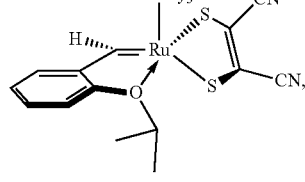
,
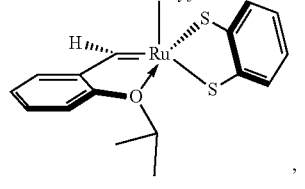
,
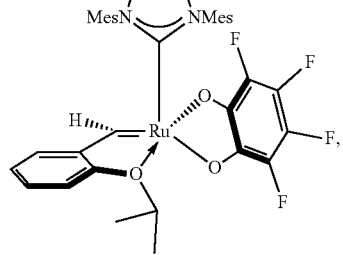
,
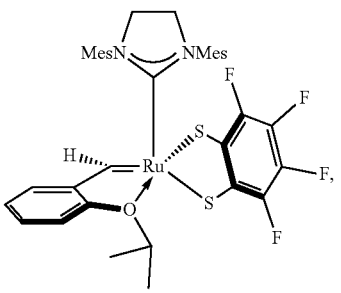
,
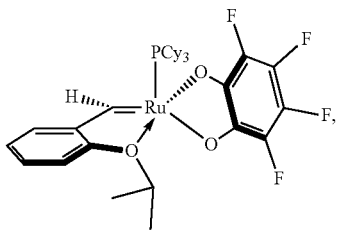
,
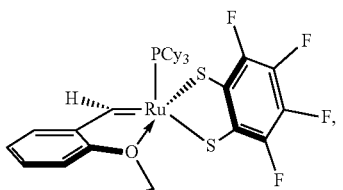
,
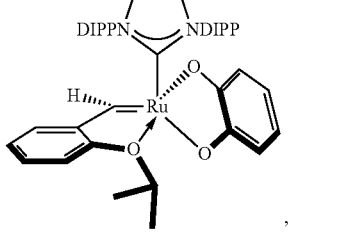
,
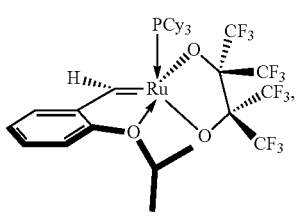
,
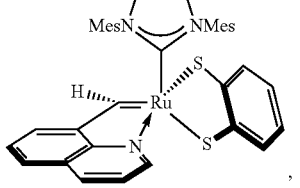
,
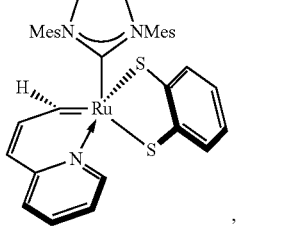
,

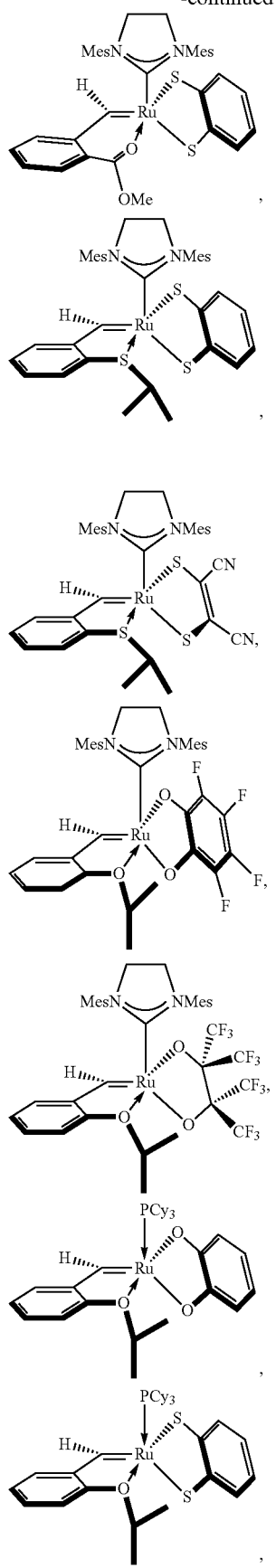

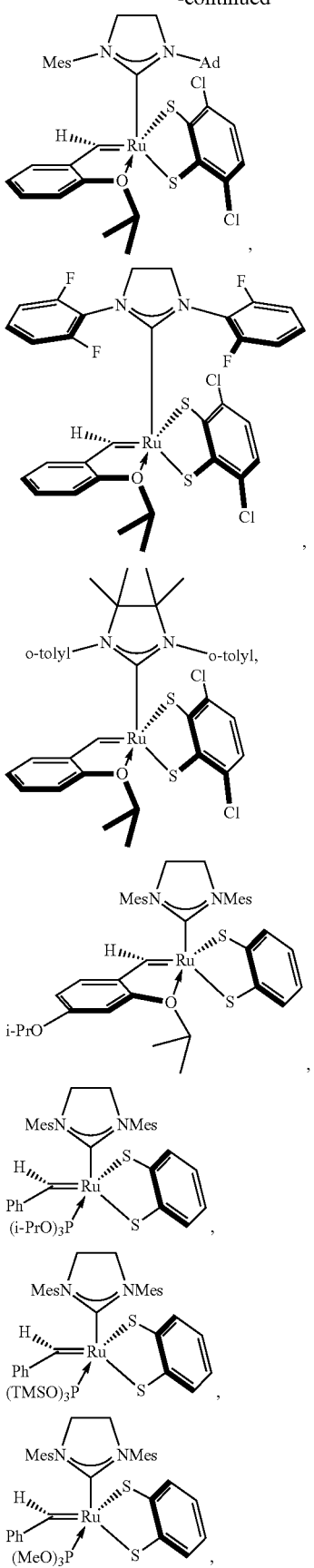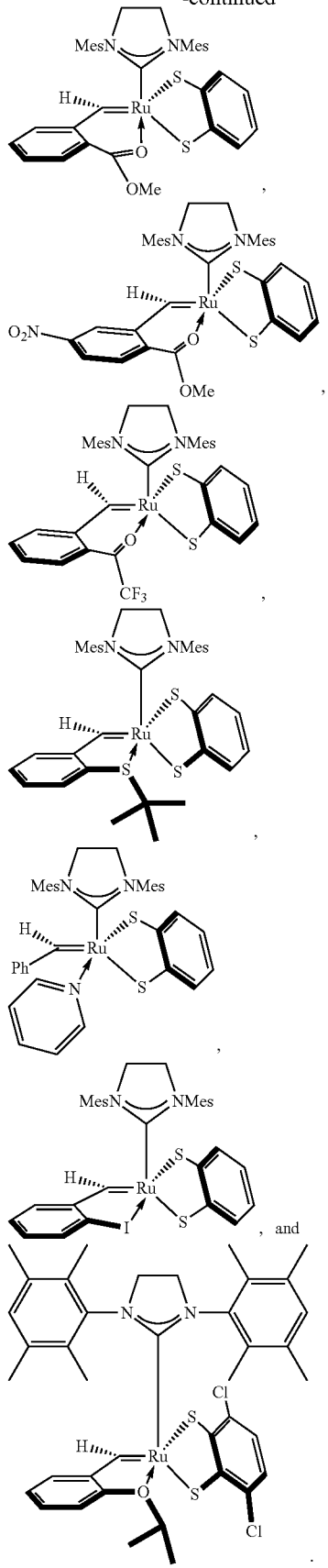

(Mes=mesityl; Cy=cyclohexyl; DIPP=diisopropyphenyl; TBS=tert.-butyldimethylsilyl; mes=mesitylene; Ad=1-adamantyl; Ph=phenyl; TMS=trimethylsilyl; Me=methyl; Pr=propyl).

DETAILED DESCRIPTION OF THE INVENTION

The invention relates to a method of making a second olefin using a first olefin, comprising steps (A) and (B):
(A) performing a metathesis reaction with the first olefin in the presence of a metal complex configured to catalyse said metathesis reaction in order to obtain a reaction mixture containing an olefin;
(B) epoxidizing the olefin contained in the reaction mixture obtained in step (A) to form an epoxide; and deoxygenizing said epoxide to form said second olefin.

According to step (A) of the method according to the invention, a metathesis reaction is performed with a first olefin in the presence of a metal complex configured to catalyse said metathesis reaction wherein a reaction mixture is obtained which contains an olefin.

The term "olefin" as used herein encompasses in its broadest meaning any olefin. Said olefin may be a terminal or an internal olefin. The olefin may be acyclic or may be cyclic.

The olefin may bear one or more functional groups. Functional groups are e.g. ester groups, ether groups, amido groups, halogen groups, etc. Since it is known that sometimes metal complexes configured to catalyse a metathesis reaction do not tolerate hydroxyl groups, carboxylic groups or aldehyde groups, such groups may be provided in a protected form, if necessary and possible.

The first olefin can be any olefin.

In a particular embodiment according to the first aspect of the invention as set out in the following, said olefin is an internal olefin. In one embodiment, said first olefin may be an acyclic or a cyclic olefin.

In a further particular embodiment according to the second aspect of the invention as set out in the following, said olefin may be a terminal or an internal olefin.

Metal complexes configured to catalyse an olefinic metathesis reaction are known in the art. The person skilled in the art is capable of selecting suitable metal complexes based on the common general knowledge.

The term "metal complex" encompasses oxides, imides, coordination compounds or oxides and imides bearing in addition one or more ligands. The metal complex may be a homogeneous or a heterogeneous catalyst.

In one embodiment, said catalysts are based on molybdenum, tungsten or ruthenium.

First Aspect

In a preferred embodiment, the first olefin in the form of an internal olefin comprises an E-isomer and a Z-isomer of the first olefin. Thus, said first olefin is provided in step (A) in the form of a mixture comprising its E-isomer and its Z-isomer.

In a preferred embodiment, the ratio of the E-isomer to the Z-isomer is at least 1:1. In a preferred embodiment, the E-isomer predominates the Z-isomer.

In one embodiment, the ratio of the E-isomer to the Z-isomer is in the range of from 1:1 or greater than 1:1. In one embodiment, the ratio is from 1:1 to 9:1, preferably from 2:1 to 9:1.

In a preferred embodiment, wherein said second olefin is said Z-isomer, the method further comprises the enrichment of the E-isomer over the Z-isomer, and the subsequent conversion of the E-isomer into the Z-isomer to form the second olefin, wherein step (A) comprises step (A1):
(A1) subjecting the first olefin comprising a mixture of the E-isomer and the Z-isomer to a cross metathesis reaction with a third olefin in the presence of a metal complex configured to favour the reaction of said third olefin with said Z-isomer over the reaction of said third olefin with said E-isomer.

Thus, when using appropriate catalysts, the Z-isomer of the first olefin reacts faster with the third olefin than the E-isomer with said third olefin. Accordingly, the E-isomer is enriched since the Z-isomer reacts while the E-isomer remains substantially unreacted. Such a catalyst may be termed as a Z-selective catalyst.

Basically, as third olefin said olefin an internal or a terminal olefins or acyclic or cyclic olefins may be used.

In a preferred embodiment, said third olefin is a $C_{2-10}$ olefin, preferably a terminal $C_{2-10}$ olefin. Terminal $C_{2-10}$ olefins are preferably ethylene, propylene, 1-butene, 1-pentene, or 1-hexene.

In a particularly preferred embodiment, said third olefin is ethylene or propylene.

In a still more preferred embodiment, said third olefin is ethylene. Accordingly, in this embodiment, the first olefin is subjected to ethenolysis.

The substantially unreacted E-isomer and the metathesis products obtained from the Z-isomer in reaction with the third olefin normally have different physical properties such as different boiling points. Accordingly, the E-isomer may be isolated by distillation in a stereoisomeric pure or nearly pure form and high yield.

Accordingly, the method according to the invention may further comprise step (A2):
(A2) separating off the E-isomer enriched in step (A1).

A method of subjecting a mixture of olefinic E- and Z-isomers to metathesis in order to remove or degrade the Z-isomer by means of a Z-selective catalyst by ethenolysis has been described in the scientific literature (Marinescu, S. C., et al, "Isolation of Pure Disubstituted E Olefins through Mo-Catalyzed Z-selective Ethenolyis of Stereomeric Mixtures", J. Am. Soc. 2011, 133, 11512-11514). The inventors of the present invention discovered that also tungsten-based complexes as disclosed herein are suitable for performing Z-selective degradation of the Z-isomer.

According to the invention, the isolated E-isomer is converted to the respective Z-isomer. Further according to the invention, the E-isomer is subjected to step (B), i.e. to epoxidation in order to form an epoxide. Subsequently, said epoxide is deoxygenized to form said second olefin in the form of the Z-isomer.

For epoxidation, any method may be used which is commonly used in order to make an epoxide from an olefin.

In a preferred embodiment, epoxidation is performed using peroxy carboxylic acids such as meta-chloroperbenzoic acid. Mixtures of formic acid or acetic acid with hydrogen peroxide may also be used.

Subsequently to the epoxidation, the formed epoxide is deoxygenated. In one embodiment, this is performed such that the epoxide ring is opened by hydrolysis to form a diol. Ring opening may be performed either under acidic or basic conditions. Upon ring opening, initially a diol is formed in which the diol groups are in anti-position with respect to the original double bond of the olefin which is subjected to epoxidation.

In an alternative embodiment, the epoxide ring is opened by alcoholysis to form a beta-hydroxy ether. Preferably, methanol or ethanol is used for ring opening. Upon ring opening, initially a beta-hydroxy ether is formed in which the hydroxyl group and the ether group are in anti-position with respect to the original double bond of the olefin which is subjected to epoxidation.

Subsequently to the ring opening, the diol groups or the hydroxyl group and the ether group are reacted with a suitable agent to form a 1,3-dioxolan. When doing this, the diol or the beta-hydroxy ether has to adopt a configuration in which the hydroxyl groups or the hydroxyl group and the ether group are in a syn-position. This step determines the later configuration of the second olefin in the form of its Z-isomer, contrary to the E-isomer which is subjected in step (B1) to epoxidation.

Subsequently to the 1,3-dioxolan formation, the 1,3-dioxolan structure is degraded in a syn elimination to form the desired second olefin in the form of the Z-isomer.

Thus, the conversion of the diol or the beta-hydroxy ether into the olefin follows a reaction which is known as Corey-Winter reaction (see e.g. Block, E., "Olefinic Synthesis by Deoxygenation of Vicinal Diols", Organic Reactions 1984, Vol. 30, pages 457 to 566).

Accordingly, in a first approach, the diol obtained in step (B2) is reacted with thiophosgen or 1,1'-thiocarbonyldiimidazole to a 1,3-dioxolan in the form of a 2-thio-1,3-dioxolan. Subsequently, said dioxolan is reacted with a trialkylphosphite such as trimethylphosphite to yield the second olefin as Z-isomer and trialkylthiophosphate and carbondioxide.

In a second approach, the diol or beta-hydroxy ether obtained in step (B2) may be reacted with an ortho ester to yield the respective 1,3-dioxolane. Preferably, the ortho carboxylic acid ester has the formula $HC(OR')_3$ wherein R' is selected from the group consisting of a methyl and ethyl residue.

Other ortho esters such as the ortho esters of acetic acid and benzoic acid may be employed, too. Accordingly, in one embodiment, the ortho ester has the formula $R''C(OR')_3$ wherein R' is selected from the group consisting of a methyl and ethyl residue, and R" is H, $CH_3$ or $C_6H_5$.

Subsequently to the 1,3-dioxolane formation, the 1,3-dioxolane structure is degraded by pyrolysis in a syn elimination to form the desired second olefin in the form of the Z-isomer.

In one embodiment, it is not necessary to isolate said 1,3-dioxolane. Rather, the diol or beta-hydroxy ether may be converted into the Z-isomer without isolation of the 1,3-dioxolane.

Accordingly, the method of the invention according to the first aspect further comprises converting the E-isomer enriched in step (A1) or separated off in step (A2) to the Z-isomer, the conversion comprising steps (B1) to (B4):

(B1) epoxidizing said E-isomer;
(B2) subjecting the epoxide obtained in step (B1) to hydrolysis to form a diol or to alcoholysis to form a beta-hydroxy ether;
(B3) converting the diol or the beta-hydroxy ether obtained in step (B2) to a 1,3-dioxolane;
(B4) degrading the 1,3-dioxolane obtained in step (B3) (in a syn elimination) to form the second olefin in the form of its Z-isomer.

Said E-isomer to be oxidized in step (B1) is said olefin in the reaction mixture obtained in step (A), respectively step (A1).

In one embodiment, step (B3) comprises the reaction of the diol obtained in step (B2) with thiophosgen or 1,1'-thiocarbonyldiimidazol; and step (B4) comprises the reaction with a trialkylphosphite.

In another embodiment, step (B3) comprises the reaction of the diol obtained in step (B2) with an ortho ester; and step (B4) comprises the pyrolysis of the formed 1,3-dioxolane.

In still another embodiment, step (B3) comprises the reaction of the beta-hydroxy ether obtained in step (B2) with an ortho ester; and step (B4) comprises the pyrolysis of the formed 1,3-dioxolane.

In a preferred embodiment, the first olefin used in step (A) or step (A1) is a 9-dodecenoate, preferably the methyl ester, and comprises a mixture of the E- and Z-isomer, preferably in a ratio of about 80% E-isomer to 20% Z-isomer.

Then, a metathesis reaction of the first olefin with the third olefin according to step (A) or (A1) is performed, the third olefin being preferably in the form of a $C_{2-10}$ olefin, preferably a terminal $C_{2-10}$ olefin, and further preferably ethylene. Subsequently, the enriched E-isomer is subjected to deoxygenation according to step (B), i.e. sub-steps (B1) to (B4). As a result, the second isomer, i.e. the Z-isomer may be obtained having a stereoisomeric purity of more than 95%.

Second Aspect

In a preferred embodiment of the second aspect, the first olefin comprises an E-isomer and a Z-isomer of the olefin. Thus, said first olefin is provided in step (A) in the form of a mixture comprising its E-isomer and its Z-isomer.

In one embodiment, the Z-isomer predominates the E-isomer.

In one embodiment, the ratio of the Z-isomer to the E-isomer is at least 9:1.

According to the second aspect, step (A) comprises step (A11):

(A11) subjecting the first olefin to a cross metathesis reaction with a fourth olefin in the presence of a metal complex to form a fifth olefin, wherein the metal complex is configured to favour the formation of the Z-isomer over the formation of the E-isomer of the fifth olefin.

Metal complex being configured to favour the formation of the Z-isomer over the formation of the E-isomer in olefin metathesis are known in the art. Such complexes may be termed as Z-selective complexes.

The metal complexes disclosed in WO 2014/201300, WO 2011/040963, WO 2014/172534 and WO 2013/070725 as referred to in the Background section may be used to catalyse step (A11).

The Z-isomer may then be epoxidized. Subsequently, the generated epoxide is deoxygenized using steps as referred to in the first aspect.

Thus, the method further comprises the subsequent conversion of the Z-isomer into the E-isomer to form the second isomer, wherein step (B) comprises steps (B11) to (B14):

(B11) epoxidizing said Z-isomer;
(B12) subjecting the epoxide obtained in step (B11) to hydrolysis to form a diol or to alcoholysis to form a beta-hydroxy ether;
(B13) converting the diol or beta-hydroxy ether obtained in step (B12) to a 1,3-dioxolane;
(B14) degrading the 1,3-dioxolane obtained in step (B13) to form the second olefin in the form of the E-isomer.

Said Z-isomer to be oxidized in step (B11) is said olefin contained in the reaction mixture obtained in step (A), respectively step (A11).

The fourth olefin may be an internal or terminal olefin, or an acylic or cyclic olefin.

The first and the fourth olefin may be different from one another or may be identical.

In one embodiment, the first olefin and the fourth olefin are identical. Accordingly, a homo cross metathesis is performed.

In a preferred embodiment, the first and the fourth olefin are identical and are a 9-decenoate, preferably the methyl ester.

Catalysts

Basically, any catalyst may be used in step (A) provided it is configured to catalyse an olefinic metathesis reaction.

Suitable catalysts are preferably catalysts based on tungsten, molybdenum and ruthenium oxides, salts and complexes.

Step (A1) mandatorily requires the use of a catalyst which favours the reaction of the Z-isomer with the third olefin, i.e. preferably with the terminal $C_{2-10}$ olefin, over the reaction of the E-isomer with said third olefin. Accordingly, the use of a Z-selective catalyst is required. In one embodiment, metal complexes may be used as disclosed in the above Marinescu reference.

Step (A11) requires the use of Z-selective catalysts, i.e. catalysts which favour the formation of the Z-isomer in a metathesis reaction. In one embodiment, the catalysts known from WO 2014/201300, WO 2011/040963, WO 2014/172534 and WO 2013/070725 as referred to in the Background section may be used.

In a preferred embodiment, the catalysts used in step (A1) and step (A11) may be the same since it is known that a catalyst which is highly Z-selective when forming a cross product [such as in step (A11)] is expected to also be able to selectively degrade Z-olefins by ethenolysis (see Miyazaki, H. et al., "Z-selective Ethenolysis with a Ruthenium Metathesis Catalyst: Experiment and Theory", J. Am. Chem. Soc. 2013, 135(15), 5848-5858).

In one embodiment, Z-selective metal complexes used in step (A1) and step (A11) have in common that they are molybdenum or tungsten alkylidene complexes comprising an imido group or an oxo group, an aryloxy ligand and a N-heterocyclic ligand.

Accordingly, in one embodiment, the metal complex being configured to favour the reaction of said third olefin, preferably in the form of a terminal $C_{2-10}$ olefin, further preferably ethylene, with said Z-olefin over the reaction with said E-olefin as defined in step (A1), or the metal complex being configured to favour the formation of the Z-isomer over the formation of the E-isomer as defined in step (A11), is selected from a molybdenum or tungsten alkylidene complex comprising an imido group or an oxo group, an aryloxy ligand and a N-heterocyclic ligand.

Accordingly, in one embodiment, a catalyst of the following formula (I) is used:

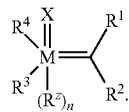
(I)

Herein,
M=Mo or W;
X=O or N—$R^5$;
$R^1$=H;
$R^2$=CMe$_3$; CMe$_2$Ph; or $C_{1-6}$ alkoxy phenyl, optionally substituted;

$R^3$=substituted aryloxy, preferably substituted phenyloxy, substituted naphthyl-2-oxy or substituted 5,6,7,8-tetrahydronaphthyl-2-oxy, or substituted naphthyl-1-oxy;
$R^4$=pyrrol-1-yl, 2,5-dimethylpyrrol-1-yl; or 2,5-diphenylpyrrol-1-yl; or substituted or unsubstituted indol-1-yl;
$R^5$=$C_{6-20}$ aryl or $C_{4-10}$ alkyl; optionally substituted.
$R^z$=neutral ligand;
n=0 or 1.

In a preferred embodiment, if X=O, M=W.
In a further preferred embodiment, if X=N—$R^5$, M=Mo or W.

The term "neutral ligand" as defined for $R^z$ encompasses any uncharged molecule which bears an electron pair that can bind to the metal center M. Preferred neutral ligands are selected from phosphines such as trialkyl such as trimethylphosphine, tricycloalkyl such as tricyclohexylphosphine or triaryl phosphines such as triphenylphosphine, ethers such as cyclic ethers such as THF or linear ethers such as diethylether, and pyridines.

The term "optionally substituted" as defined for $R^2$, wherein $R^2$ is optionally substituted $C_{1-6}$ alkoxy phenyl, encompasses substituents in the phenyl moiety selected from halogen, $C_{1-6}$ alkyl, $C_{1-6}$ alkoxy, phenyl, nitro, cyano, C(O)OC$_{1-6}$ alkyl and SO$_2$N(C$_{1-6}$alkyl)$_2$, and from two or more thereof.

In a preferred embodiment, when $R^2$=o-$C_{1-6}$-alkoxyphenyl, said residue chelates the metal center M via oxygen.

The term "substituted phenyloxy" as used for $R^3$ encompasses phenyloxy at least disubstituted in 2,6-position, wherein the substituents are selected from $C_{3-4}$ alkyl, $C_{3-4}$ alkoxy, phenyl (which in turn may be substituted with one or more of $C_{3-4}$ alkyl or halogen), and $R^4$.

The term "substituted naphthyl-2-oxy or substituted 5,6,7,8-tetrahydronaphthyl-2-oxy" as used for $R^3$ encompasses respective residues substituted with one or more of halogen, $C_{1-4}$ alkyl, $C_{1-4}$ alkoxy, silyloxy, phenyl, naphthyl (which in turn may be substituted with one or more of halogen, $C_{1-4}$ alkyl, $C_{1-4}$ alkoxy, silyloxy such as TBS) or 5,6,7,8-tetrahydronaphthyl (which in turn may be substituted with one or more of halogen, $C_{1-4}$ alkyl, $C_{1-4}$ alkoxy, silyloxy).

The term "substituted naphthyl-1-oxy" as used for $R^3$ encompasses a respective residue which may be substituted with one or more of halogen, $C_{1-4}$ alkyl, $C_{1-4}$ alkoxy, silyloxy, phenyl, naphthyl (which in turn may be substituted with one or more of halogen, $C_{1-4}$ alkyl, $C_{1-4}$ alkoxy, silyloxy).

The term "substituted indol-1-yl" as used for $R^4$ encompasses the indol-1-yl residue which may be substituted with one or more of halogen, $C_{1-6}$ alkyl, $C_{1-6}$ alkoxy, phenyl, nitro, cyano, C(O)OC$_{1-6}$ alkyl and SO$_2$N(C$_{1-6}$alkyl)$_2$, or two or more thereof.

The term "optionally substituted" as defined for $R^5$= $C_{6-20}$ aryl or $C_{4-10}$ alkyl, encompasses substituents selected from halogen, $C_{1-6}$ alkyl, $C_{1-6}$ alkoxy, phenyl, nitro, cyano, C(O)OC$_{1-6}$ alkyl and SO$_2$N(C$_{1-6}$alkyl)$_2$, or two or more thereof.

In a preferred embodiment, $C_{6-20}$ aryl=phenyl, optionally substituted. In a further preferred embodiment, phenyl is substituted in 2- and 6-position.

In another preferred embodiment, $C_{4-10}$ alkyl=tert.-butyl or 1-adamantyl.

Exemplary structures are depicted below, wherein the hydroxyl group is deprotonated upon coordination to the metal center M, and wherein residues R have independently the meaning as defined above:

Substituted phenyloxy, phenyl being at least substituted in 2,6 position such as
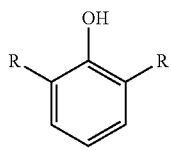
such as
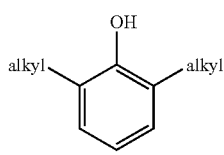
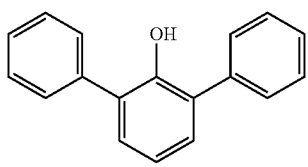
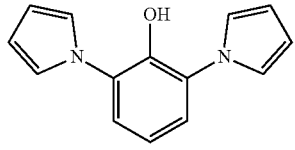 or 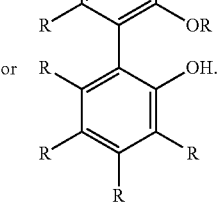
Substituted naphthyl-2-oxy and 5,6,7,8-tetrahydronaphthyl-2-oxy such as
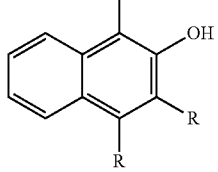   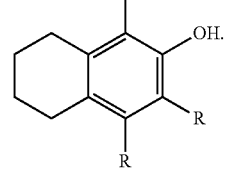
Substituted naphthyl-1-oxy such as
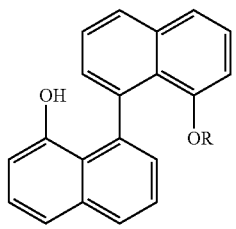
Preferred metal complexes are:
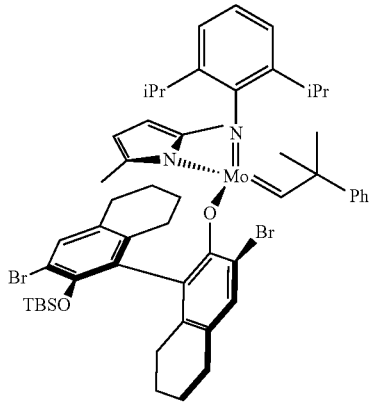
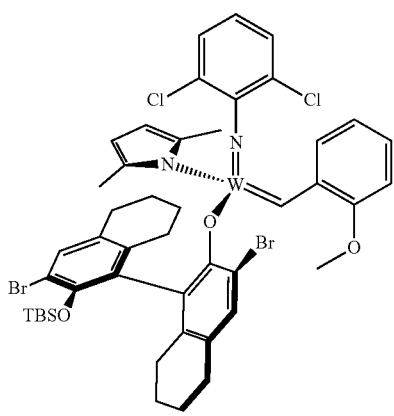
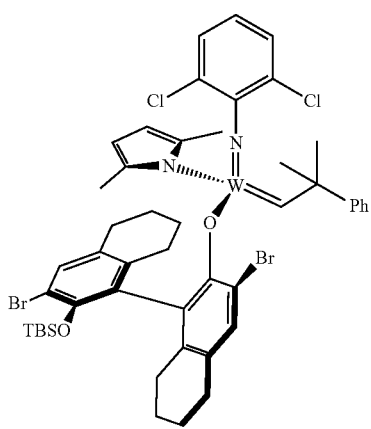

33
-continued

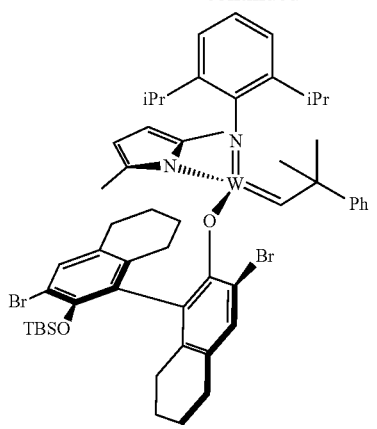

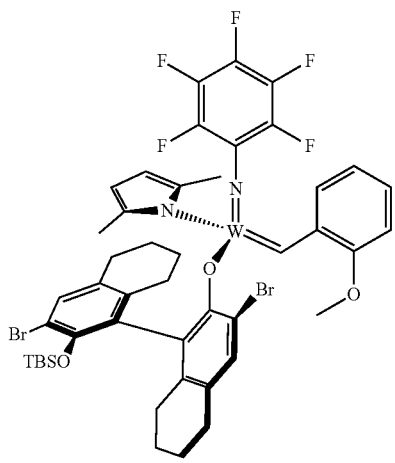

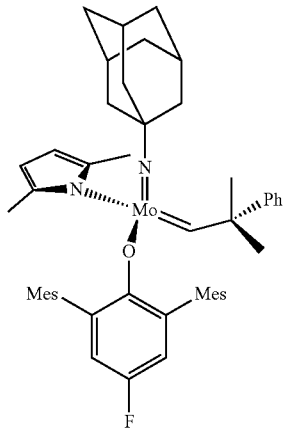

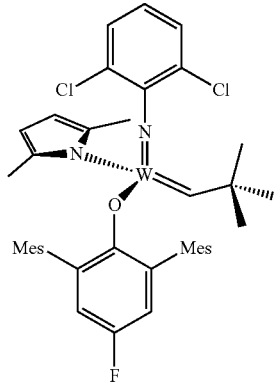

34
-continued

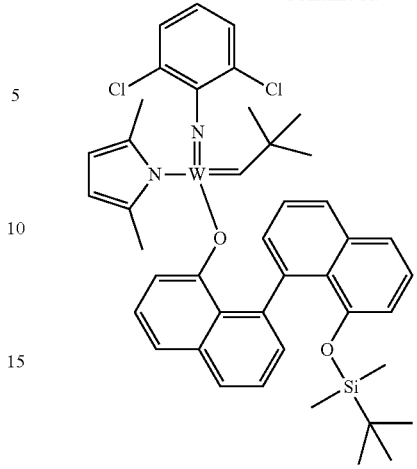

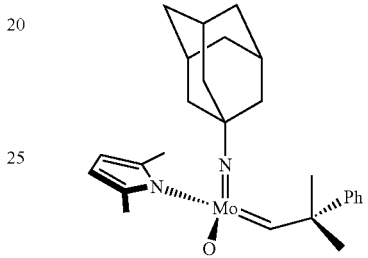

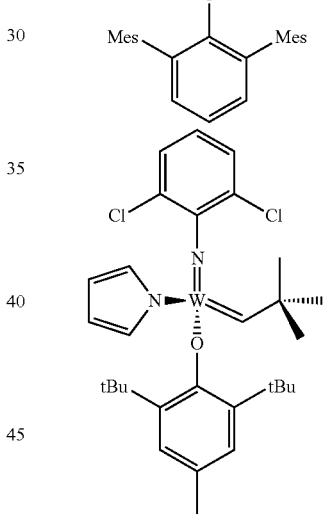

(TBS = tert.-butyldimethylsilyl; mes = mesitylene).

In a further embodiment, Z-selective metal complexes are selected from ruthenium alkylidene complexes, preferably wherein said alkylidene may form a chelate with ruthenium, and wherein further preferably the complex comprises a nitrogen-containing heterocyclic carbene.

Accordingly, in a further embodiment, the metal complex being configured to favour the reaction of said third olefin, preferably in the form of a terminal $C_{2-10}$ olefin, with said Z-olefin over the reaction with said E-olefin as defined in step (A1), or the metal complex being configured to favour the formation of the Z-isomer over the formation of the E-isomer as defined in step (A11), is selected from a ruthenium alkylidene complex, preferably wherein said alkylidene forms a chelate with ruthenium, and wherein further preferably the complex comprises a nitrogen-containing heterocyclic carbene.

Accordingly, a metal complex of the following formula (II) may be used as defined in WO 2014/201300:

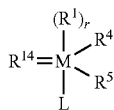
(II)

Herein,
M=Ru;
each of $R^1$ and L is a neutral ligand;
r=1-3;
each of $R^4$ and $R^5$ is independently bonded to M through sulfur or oxygen; or $R^4$ and $R^5$ are halogen, preferably Cl;
$R^{14}$ is a carbene.

The term "neutral ligand" as defined for $R^1$ and L encompasses any uncharged molecule which bears an electron pair that can bind to the metal center. Preferred neutral ligands are selected from phosphines such as trialkyl or triaryl phosphines, ethers such as cyclic ethers or linear ethers, and pyridines.

In a preferred embodiment, the neutral ligand may be a nitrogen-containing heterocyclic carbene (NHC).

The term "carbene" as used for $R^{14}$ bonded to M encompasses in a preferred embodiment the structure M=CH—$R^{15}$. $R^{15}$ may be selected from $C_{6-10}$ aryl-$CH_2$—$CH_2$—, $C_{6-10}$ heteroaryl-$CH_2$—$CH_2$—, $C_{6-10}$ aryl and $C_{6-10}$ heteroaryl, optionally substituted.

A preferred residue $R^{15}$ is o-$C_{1-6}$-alkoxyphenyl or o-$C_{1-6}$-alkylthiophenyl or o-halo-$C_6H_4$, optionally substituted. Optional substituents may be selected from halogen, $C_{1-6}$ alkyl, $C_{1-6}$ alkoxy, phenyl, nitro, cyano, C(O)O$C_{1-6}$ alkyl and SO$_2$N($C_{1-6}$ alkyl)$_2$.

A further preferred residue $R^{15}$ is o-$C_6H_4$C(O)O$C_{1-6}$ alkyl, wherein the alkyl residue may be substituted with one or more of halogen.

In a further preferred embodiment, the oxygen atom of the o-$C_{1-6}$-alkoxyphenyl residue or the sulfur atom of the o-$C_{1-6}$-alkylthiophenyl residue or the halogen of the o-halo-$C_6H_4$ or the carbonyl group of the o-$C_6H_4$C(O)O$C_{1-6}$ alkyl residue chelates the metal center M.

Preferred ruthenium complexes are presented hereinunder:

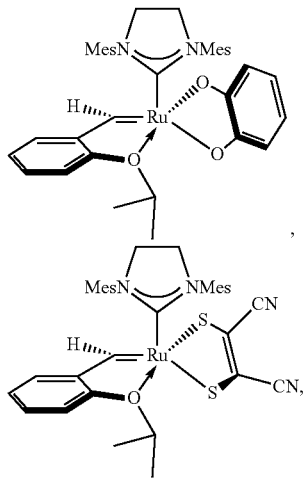

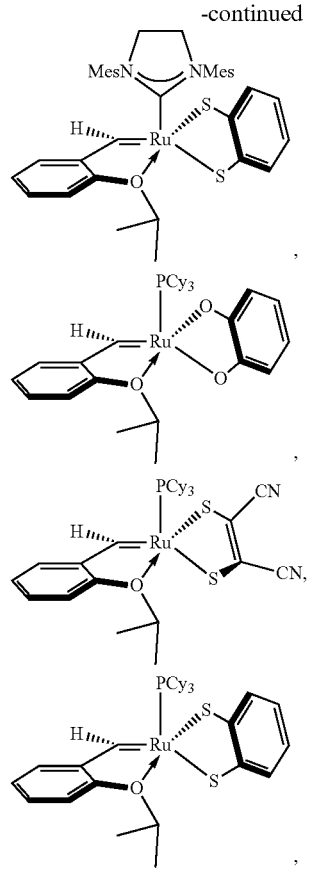

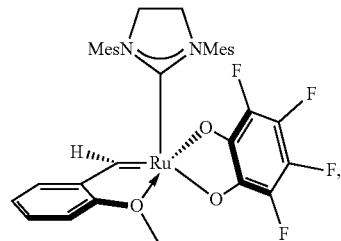

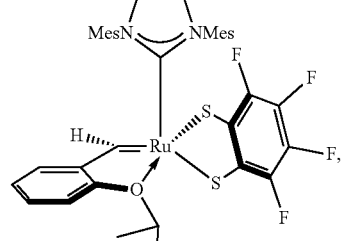

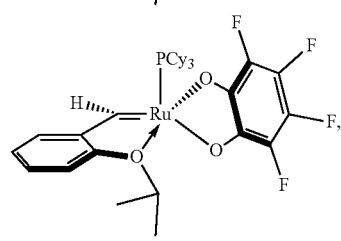

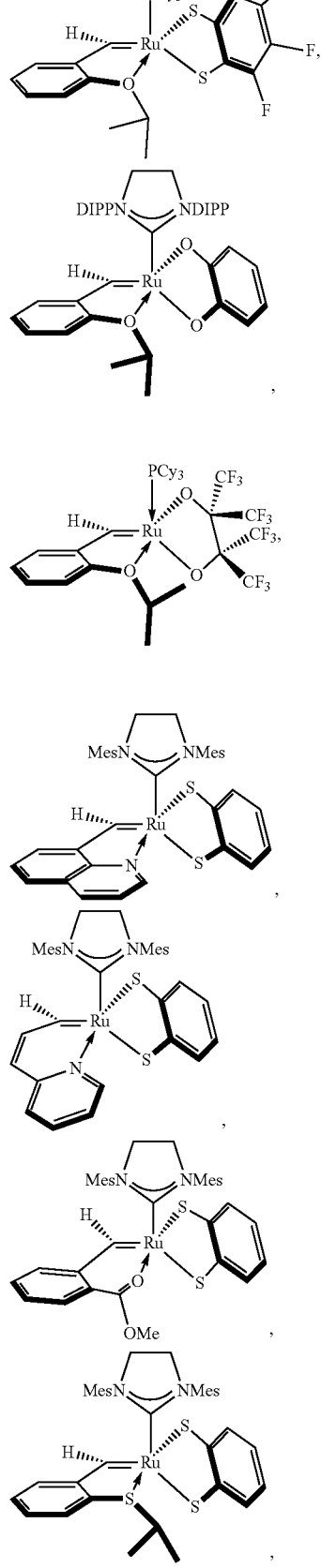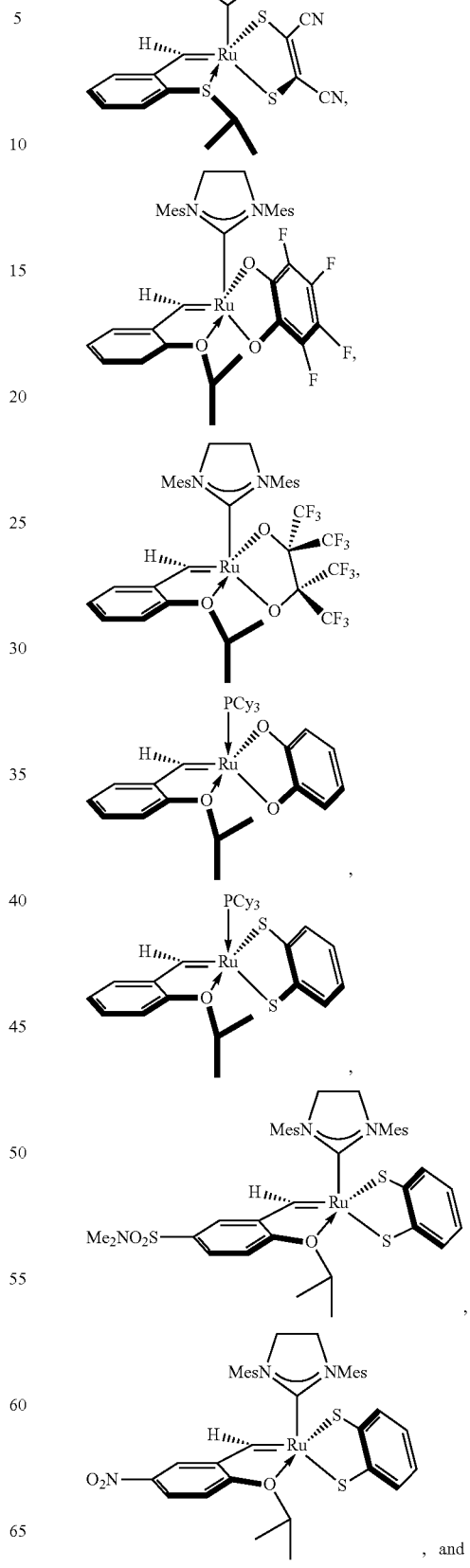

-continued
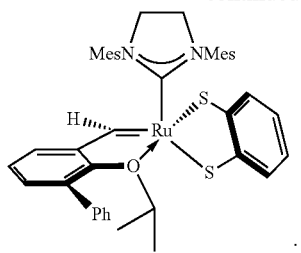
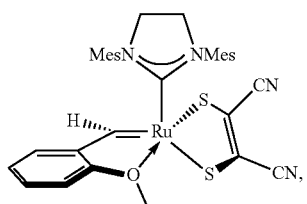
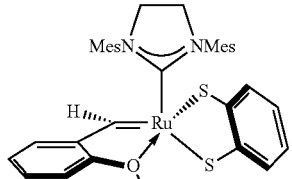
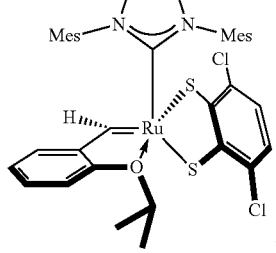
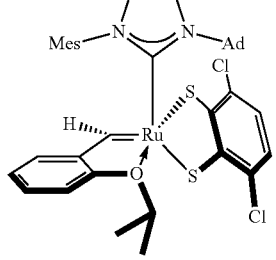
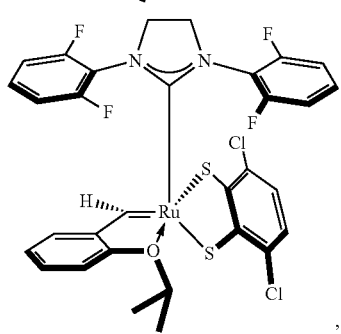
-continued
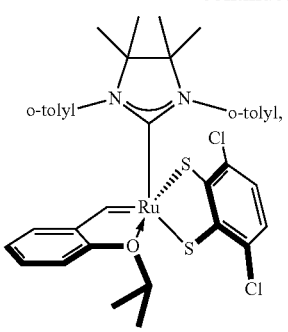
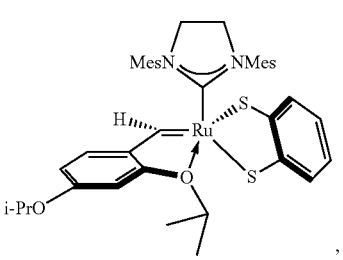
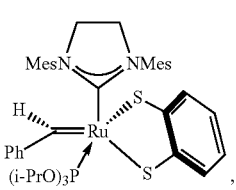
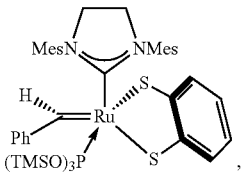
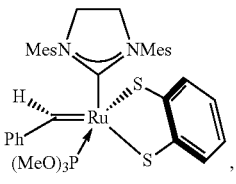
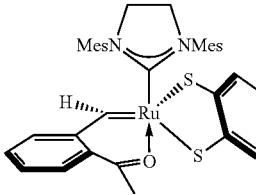
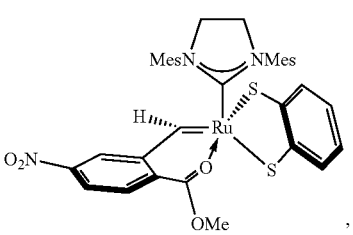

-continued

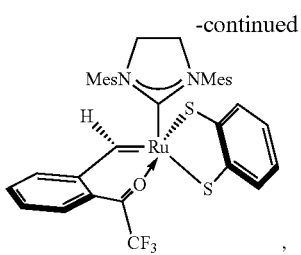

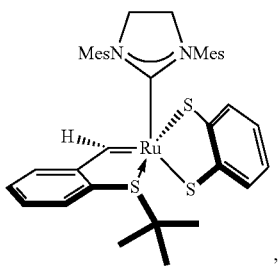

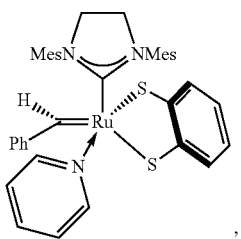

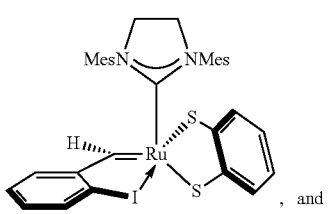, and

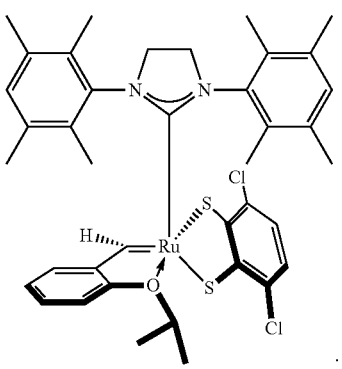

(Mes=mesityl; Cy=cyclohexyl; DIPP=diisopropyphenyl)

A ruthenium catalyst of formula (II) in which $R^4$ and $R^5$ are Cl, respectively, is

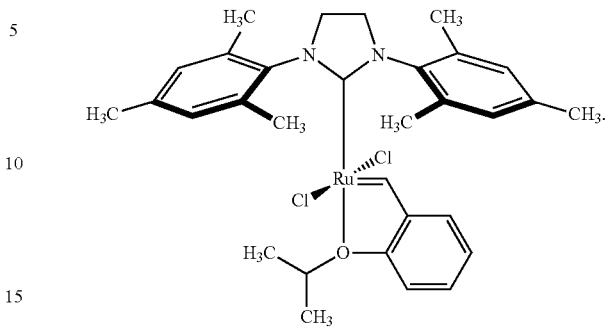

Further Z-selective ruthenium catalysts useful in step (A1) or step (A11) are of structure (III) as disclosed in WO 2012/097379:

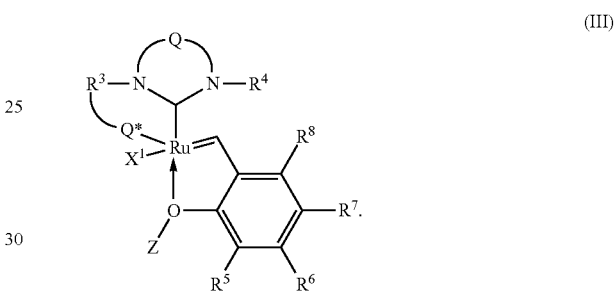

(III)

Herein,
Q=a hydrocarbylene such as an alkylene group, or alkyl-substituted hydrocarbylene;
Q* forms a carbon-ruthenium bond with the carbon from the $R^3$ group;
$X^1$ is nitrate, or $C_{1-20}$ alkylcarboxylate;
$R^3$ is cycloalkyl or an alkyl substituted cycloalkyl group;
$R^4$ is an alkyl substituted aryl group;
Z is alkyl; and
$R^5$, $R^6$, $R^7$ and $R^8$ are hydrogen.
Exemplary compounds are

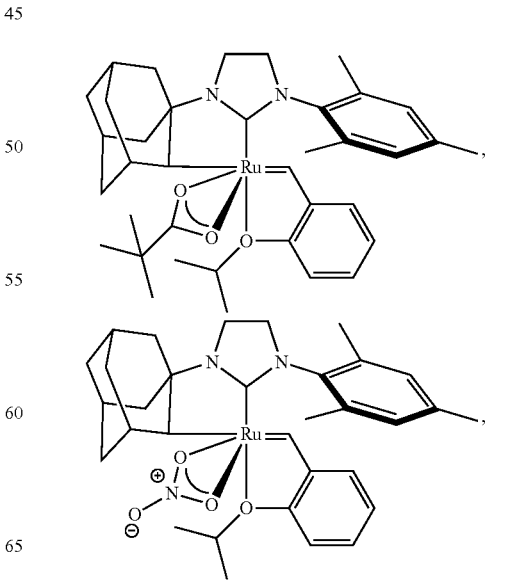

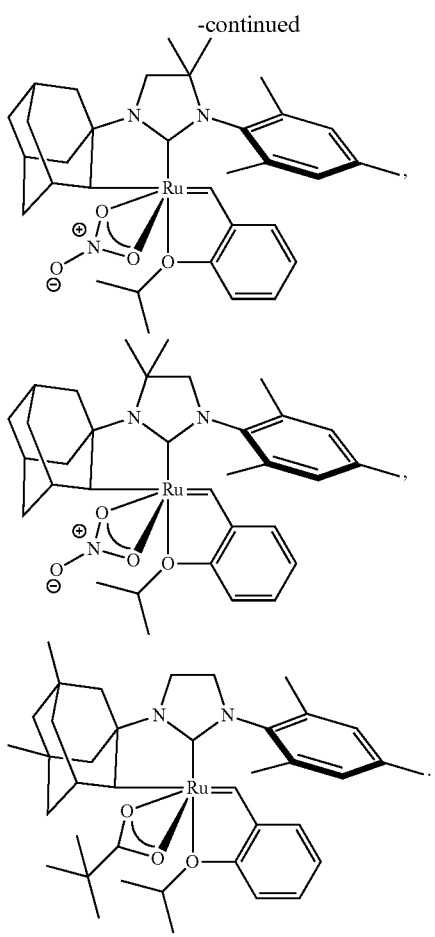

EXAMPLES

Example 1: Preparation of Methyl Z-9-Dodecenoate as Second Olefin According to the Method Defined in the First Aspect A mixture of E- and Z-isomers 1 and 2 of methyl 9-dodecenoate in the ratio of 80:20 had been obtained in a metathesis reaction. The compounds may be identified by means of nuclear magnetic resonance spectroscopy:

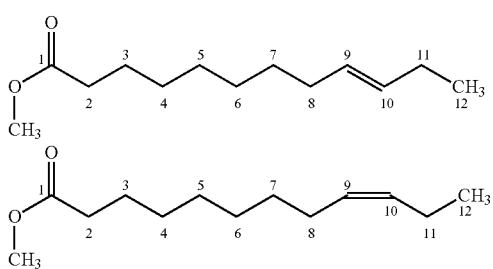

E-isomer 1

$^1$H-NMR (C$_6$D$_6$) δ: 0.96 (t, 3H, C12-H3), 1.16-1.39 (m, 8H, C4-H2, C5-H2, C6-H2, C7-H2), 1.52-1.68 (m, 2H, C3-H2), 1.98 (m, 4H, C8-H2, C11-H2), 2.10 (t, 3JHH=7.6 Hz, 2H, C2-H2), 3.36 (s, 3H, OCH3), 5.45 ppm (m, 2H, C9-H, C10-H).

$^{13}$C-NMR (C6D6) δ: 14.3 (C12), 25.3 (C3), 26.2 (C11), 29.4, 29.5, 29.6, 33.1 (C8), 34.2 (C2), 51.0 (OCH3), 129.7 (C9), 132.3 (C10), 173.4 ppm (C1).

Z-isomer 2

$^1$H-NMR (C$_6$D$_6$) δ: 0.94 (t, 3H, C12-H3), 1.16-1.39 (m, 8H, C4-H2, C5-H2, C6-H2, C7-H2), 1.52-1.68 (m, 2H, C3-H2), 2.01 (m, 4H, C8-H2, C11-H2), 2.10 (t, 3JHH=7.6 Hz, 2H, C2-H2), 3.36 (s, 3H, OCH3), 5.42 ppm (m, 2H, C9-H, C10-H).

$^{13}$C-NMR (C6D6) δ: 14.7 (C12), 21.0 (C11), 25.3 (C3), 27.6 (C8), 29.5, 29.5, 29.6, 34.2 (C2), 51.0 (OCH3), 129.6 (C9), 131.8 (C10), 173.4 ppm (C1).

This mixture was subjected according to the first aspect of the invention to Z-selective ethenolysis in order to enrich the E-isomer. Subsequently the E-isomer was converted to the Z-isomer, which was obtained in a high yield and stereoisomeric purity. The reaction sequence is depicted in the following scheme:

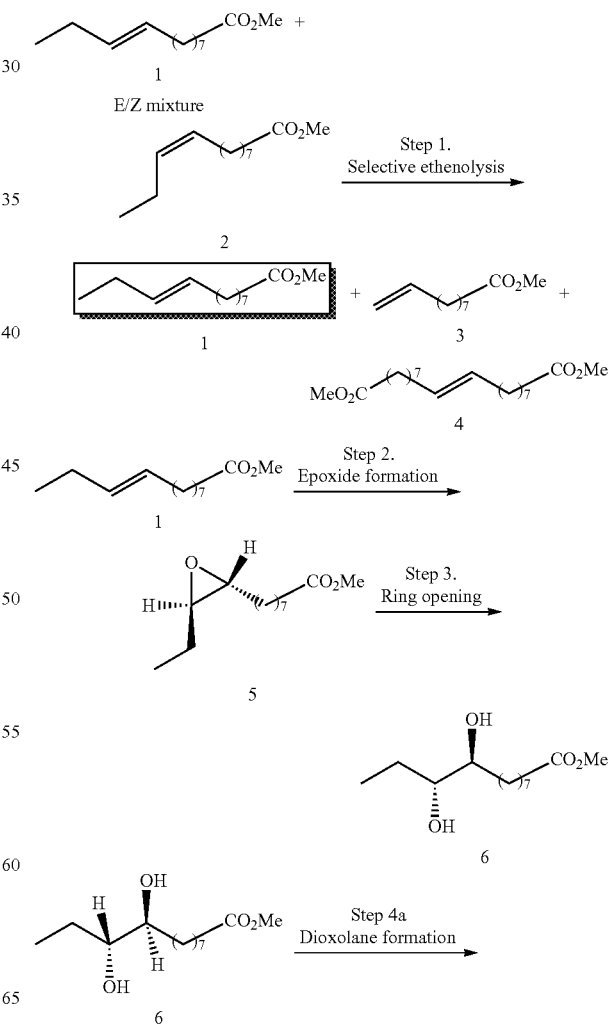

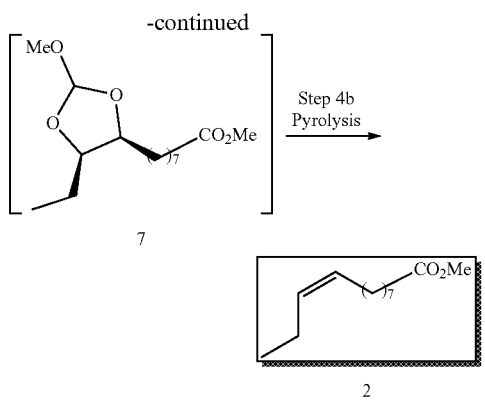

Ethenolysis of a Mixture of E- and Z-Isomers of Methyl 9-Dodecenoate 1 and 2:
The stock solution of catalyst

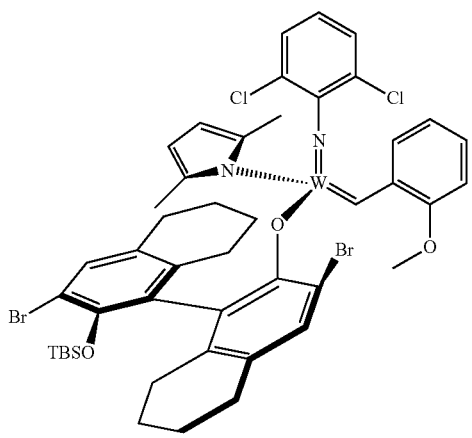

(prepared according to known methods; TBS=tert.-butyldimethylsilyl) was added to methyl 9-dodecenoate (0.45 mL, E/Z=80/20 mixture) and the reaction mixture was pressurized by 10 bar ethylene and stirred at rt for 2 h. Then the pressure was released and MeOH (4.5 ml) was added. An aliquot (200 µL) was taken out and charged onto the top of a silica gel column (0.5 ml silica gel in a 20 ml hypodermic syringe) and the components were eluted with dichloromethane (total DCM used: 25 ml). The eluate was analyzed by gas chromatography. The E-isomer 1 was obtained in a yield of approx. 80% having a stereoisomeric purity of approx. 96%. 3 is the ethenolysis product of Z-isomer 2. Compound 4 is formed as a side-product.

Synthesis of methyl 8-(3-ethyloxiran-2-yl)octanoate 5

3-Chloroperbezoic acid (mCPBA, 77% purity, 4,572 mg, 20.4 mmol) was added to a solution of methyl 9-dodecenoate 1 (4.84 ml, 20 mmol) in dichloromethane (150 mL) at 0° C. in small portions. The reaction mixture was allowed to warm at room temperature and stirred overnight. Then the reaction mixture was poured into saturated $NaHCO_3$ (100 mL) stirred and partitioned. The aqueous layer was extracted with dichloromethane (2×70 mL). The organics were washed with brine and dried over $MgSO_4$. The crude product 5 was purified by column chromatography (10 to 20% EtOAc in heptanes) resulting 2740 mg (60%) colorless liquid.

In the following, for comparison, also the respective resonances of the respective Z products/intermediates are listed:

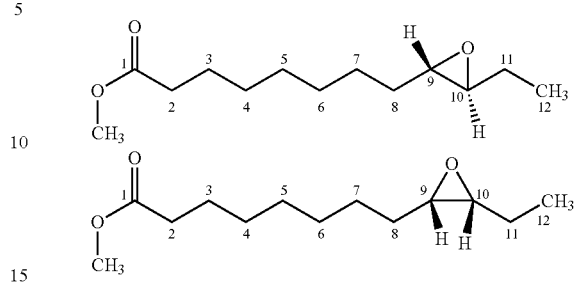

$^1$H-NMR ($C_6D_6$) of 5 (trans isomer) δ: 0.86 (t, 3H, C12-$H_3$), 1.04-1.33 (m, 8H, C4-$H_2$, C5-$H_2$, C6-$H_2$, C7-$H_2$), 1.38 (m, 4H, C8-$H_2$, C11-$H_2$), 1.54 (m, 2H, C3-$H_2$), 2.11 (t, $^3J_{HH}$=7.6 Hz, 2H, C2-$H_2$), 2.44 (m, 2H, C9-H, C10-H), 3.36 (s, 3H, $OCH_3$).
$^1$H-NMR ($C_6D_6$) (cis isomer) δ: 0.89 (t, 3H, C12-$H_3$), 1.04-1.33 (m, 8H, C4-$H_2$, C5-$H_2$, C6-$H_2$, C7-$H_2$), 1.38 (m, 4H, C8-$H_2$, C11-$H_2$), 1.54 (m, 2H, C3-$H_2$), 2.12 (t, $^3J_{HH}$=7.6 Hz, 2H, C2-$H_2$), 2.68 (m, 2H, C9-H, C10-H), 3.36 (s, 3H, $OCH_3$).

Synthesis of diastereomeric methyl (9S,10R)-9,10-dihydroxydodecanoate methyl (9S,10S)-9,10-dihydroxydodecanoate Epoxide 5 (2.74 g, 12 mmol) was dissolved in acetic acid (60 mL) and refluxed for 3 h. Then the reaction mixture was concentrated in vacuo. The residue was taken up in MeOH (50 mL) and NaOH (1.0 g, 25.2 mmol) was added. After 3 h, the reaction mixture was diluted with saturated $NH_4Cl$ solution (100 mL) and extracted with ethyl acetate (3×100 mL). The organic layer was washed with brine and dried over $MgSO_4$. The crude diol 6 was isolated as an off white solid (2.8 g, 94%)

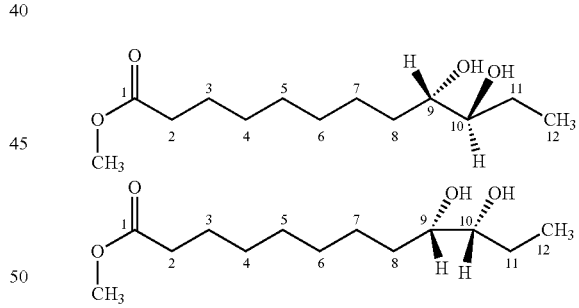

$^1$H-NMR ($C_6D_6$) of 6: δ: 0.93 (t, 3H, C12-$H_3$), 1.10-1.90 (m, 14H, C3-$H_2$, C4-$H_2$, C5-$H_2$, C6-$H_2$, C7-$H_2$, C8-$H_2$, C11-$H_2$), 2.12 (t, $^3J_{HH}$=7.6 Hz, 2H, C2-$H_2$), 3.14 and 3.24 (m, 2H, C9-H, C10-H), 3.37 (s, 3H, $OCH_3$). E-isomers (9S,10R and 89R,10S)
$^1$H-NMR ($C_6D_6$) δ: 0.93 (t, 3H, C12-$H_3$), 1.10-1.90 (m, 14H, C3-$H_2$, C4-$H_2$, C5-$H_2$, C6-$H_2$, C7-$H_2$, C8-$H_2$, C11-$H_2$), 2.12 (t, $^3J_{HH}$=7.6 Hz, 2H, C2-$H_2$), 3.27 and 3.38 (m, 2H, C9-H, C10-H), 3.37 (s, 3H, $OCH_3$). Z-isomers (9S,10S and 9R,10R)

Synthesis of methyl Z-9-dodecenoate 2

Diol 6 (730 mg, 3.0 mmol) was dissolved in triethylorthoformate (1.1 mL), benzoic acid (0.3 mmol, 37 mg) was added to it and the mixture was heated at 70° C. for 1 h, then at 100° C. for another hour. Then the reaction mixture was concentrated in vacuo, benzoic acid (0.45 mmol, 55 mg) was added and the mixture was stirred at 200° C. for 8 h (gas evolution). The mixture was separated by column chromatography (10% EtOAc in heptanes) resulting in 492 mg (77%) colorless liquid.

Purity by GC: 95%

Example 2: Preparation of Methyl E-9-Octadecenedioic Acid Methyl Ester as Second Olefin According to the Second Aspect Methyl 9-decenoate was subjected to a Z-selective homo cross metathesis reaction. The formed Z-product was subsequently converted to the E-isomer. The reaction is depicted in the following scheme:

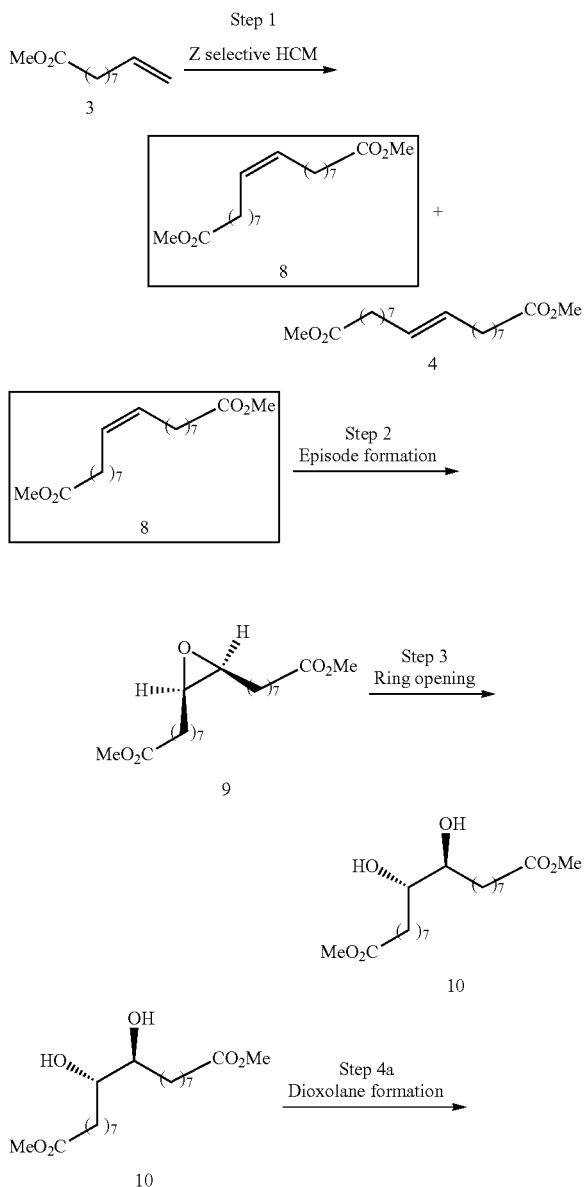

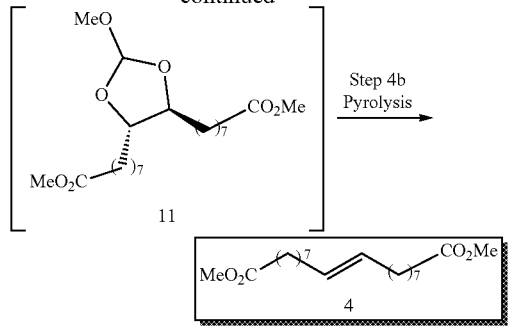

Z-Selective Homo-Cross Metathesis of Methy 9-Decenoate 3

Methyl 9-decenoate 3 was subjected to Z-selective homo-cross metathesis according to the method disclosed by Jiang, Annie J. et al, Highly Z-Selective Metathesis Homocoupling of Terminal Olefins, J. Am. Chem. Soc., 131(46), 16630-16631; 2009.

Resulting methyl 9-octadecenedioic acid methyl ester in the form of its Z-isomer 8 and E-isomer 4 were obtained in a ratio of approx. 95:4.

Synthesis of (methyl 8-[3-(8-methoxy-8-oxooctyl) oxiran-2-yl]octanoate) 9

3-Chloroperbezoic acid (mCPBA) (77% purity, 2.28 g, 10.2 mmol) was added to a solution of methyl 9-octadecenedioate (Z/E ratio 95/5, 3.51 g, 10 mmol, Z/E ratio=95/5) in dichloromethane (75 mL) at 0° C. in small portions. The reaction mixture was allowed to warm at room temperature and stirred overnight. The reaction mixture was poured into saturated NaHCO$_3$ (50 mL), stirred and partitioned. The aqueous layer was extracted with dichloromethane (2×50 mL). The organics were washed with brine and dried over MgSO$_4$. The crude product was purified by column chromatography (10 to 20% EtOAc in heptanes) resulting in 3020 mg (84%) colourless liquid:

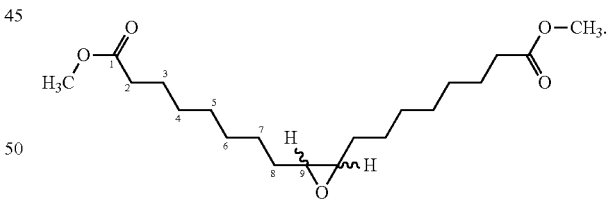

$^1$H-NMR (C$_6$D$_6$) δ: 1.05-1.48 (m, 20H, C4-H$_2$, C5-H$_2$, C6-H$_2$, C7-H$_2$, C8-H$_2$), 1.54 (m, 4H, C3-H$_2$), 2.11 (t, $^3J_{HH}$=7.6 Hz, 4H, C2-H$_2$), 2.75 (m, 2H, C9-H), 3.37 (s, 6H, OCH$_3$).

Synthesis of diastereomeric diol (methyl (9S,10R)-9,10-dihydroxydodecanoate methyl (9S,10S)-9,10-dihydroxydodecanoate 10

The epoxide 9 (3.02 g, 8.5 mmol) was dissolved in acetic acid (28 mL), allowed to stand overnight, and was then refluxed for 3 h. Then the reaction mixture was concentrated in vacuo. The residue was taken up in MeOH (30 mL) and NaOH (475 mg, 11.9 mmol) was added. The course of the reaction was monitored as above. After 3 h, the reaction mixture was diluted with saturated NH₄Cl solution (100 mL) and extracted with ethyl acetate (3×50 mL). The organic layer was washed with brine and dried over MgSO₄. The crude product was isolated as a white solid (2.95 g, 93%):

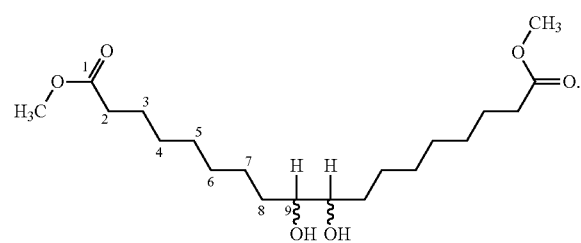 [SMILES: COC(=O)CCCCCCCC(O)C(O)CCCCCCCC(=O)OC]

¹H-NMR (C₆D₆) δ: 1.06-1.51 (m, 20H, C4-H₂, C5-H₂, C6-H₂, C7-H₂, C8-H₂), 1.57 (m, 2H, C3-H₂), 1.89 (br, 2H, OH), 2.12 (t, ³J$_{HH}$=7.6 Hz, 2H, C2-H₂), 3.27 (m, 2H, C9-H), 3.37 (s, 3H, OCH₃).

Dioxolane Formation methyl 8-[2-methoxy-5-(8-methoxy-8-oxooctyl)-1,3-dioxolan-4-yl]octanoates 11

The diol 10 (2.95 g, 7.88 mmol) was dissolved in triethylorthoformate (7 mL). A catalytic amount of benzoic acid (96 mg, 0.788 mmol) was added and the mixture was stirred at 70° C. for 3 h and then at 100° C. for 1 h. Then the mixture was evaporated to dry and washed with 5% aq. NaOH solution, 5% aq. citric acid solution and water, and then evaporated to dry. The crude product was isolated as a transparent oil (2.64 g, 80%).

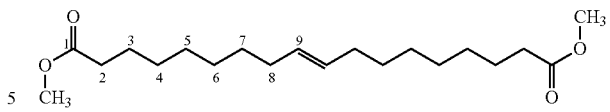

¹H NMR consistent:
¹H-NMR (C6D6) δ (ppm): 1.09-1.26 (m, 16H, C4-H2, C5-H2, C6-H2), 1.32 (m, 4H, C7-H2), 1.55 (qui, 4H, C3-H2), 2.01 (m, 4H, C8-H2), 2.11 (t, 3JHH=7.6 Hz, 4H, C2-H2), 3.37 (s, 6H, OCH3), 5.47 ppm (m, 2H, C9-H).
¹³C-NMR (C6D6) δ (ppm): 25.3 (C3), 29.4, 29.5, 29.6, 33.1 (C8), 34.2 (C2), 51.0 (OCH3), 130.8 (C9), 173.4 ppm (C1).
Z-isomer
¹H-NMR (C6D6) δ (ppm): 1.09-1.26 (m, 16H, C4-H2, C5-H2, C6-H2), 1.32 (m, 4H, C7-H2), 1.55 (qui, 4H, C3-H2), 2.06 (m, 4H, C8-H2), 2.11 (t, 3JHH=7.6 Hz, 4H, C2-H2), 3.37 (s, 6H, OCH3), 5.46 ppm (m, 2H, C9-H).
¹³C-NMR (C6D6) δ (ppm): 25.3 (C3), 27.7 (C8), 29.5, 29.5, 29.6, 34.2 (C2), 51.0 (OCH3), 130.2 (C9), 173.4 ppm (C1).

The invention claimed is:
1. A method of making a second olefin using a first olefin, comprising steps (A) and (B):
   (A) performing a metathesis reaction with the first olefin in the presence of a metal complex configured to catalyze said metathesis reaction in order to obtain a reaction mixture containing an olefin; and
   (B) epoxidizing the olefin contained in the reaction mixture obtained in step (A) to form an epoxide, and deoxygenizing said epoxide to form said second olefin;

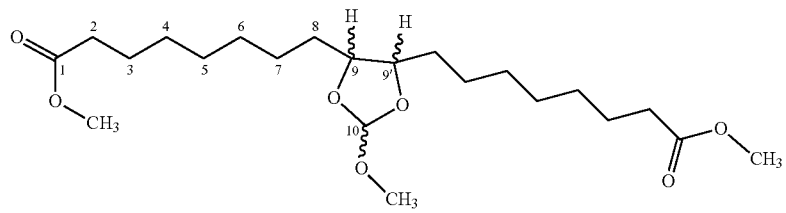 [SMILES: COC(=O)CCCCCCCC1OC(OC)OC1CCCCCCCC(=O)OC]

¹H-NMR (C₆D₆) δ: 1.06-1.73 (m, 24H, C3-H₂, C4-H₂, C5-H₂, C6-H₂, C7-H₂, C8-H₂), 2.11 (t, ³J$_{HH}$=7.6 Hz, 4H, C2-H₂), 3.17 (s, 3H, OCH₃), 3.37 (s, 6H, OCH₃), 3.61 (m, 1H, C9-H), 3.85 (m, 1H, C9'-H), 5.85 (s, 1H, C10-H).

Synthesis of methyl E-9-octadecenedioate 4

Benzoic acid (0.15 equiv, 0.951 mmol, 116 mg) was added to the crude methyl 8-[2-methoxy-5-(8-methoxy-8-oxooctyl)-1,3-dioxolan-4-yl]octanoate (11) (2.64 g, 6.34 mmol) formed in the previous step. The mixture was stirred at 200° C. for 8 h then purified by column chromatography using 0 to 20% EtOAc in heptanes. The product was isolated as a transparent oil (1.566 g, 68%, Isomer ratio: E isomer=96%, Z isomer=4%):

wherein the first olefin comprises an E-isomer and a Z-isomer of the olefin; wherein the ratio of the E-isomer to the Z-isomer in the first olefin is in the range of from 1:1 to 9:1;
wherein said second olefin is said Z-isomer, further comprising enrichment of the E-isomer over the Z-isomer, and subsequent conversion of the E-isomer into the Z-isomer to form the second olefin, wherein step (A) comprises step (A1):
   (A1) subjecting the first olefin comprising a mixture of the E-isomer and the Z-isomer to a cross metathesis reaction with a third olefin in the presence of the metal complex, wherein the metal complex is configured to favour reaction of said third olefin with said Z-isomer over the reaction of said third olefin with said E-isomer, wherein said third olefin is a C$_{2-10}$ olefin;

and further comprising conversion of the E-isomer enriched in step (A1) to the Z-isomer, the conversion comprising steps (B1) to (B4):

(B1) epoxidizing the E-isomer to form the epoxide;

(B2) subjecting the epoxide obtained in step (B1) to hydrolysis to form a diol, or alcoholysis to form a beta-hydroxy ether;

(B3) converting the diol or beta-hydroxy ether obtained in step (B2) to a 1,3-dioxolane; and (B4) degrading the 1,3-dioxolane obtained in step (B3) to form the second olefin in the form of its Z-isomer; and wherein the metal complex is selected from a compound of formula (I):

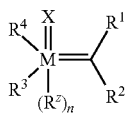
(I)

wherein
M=Mo or W
X=O or N-$R^5$;
$R^1$=H·
$R^2$=CMe$_3$; CMe$_2$Ph; or o-C$_{1-6}$-alkoxyphenyl, optionally substituted;
$R^3$=substituted aryloxy;
$R^4$=pyrrol-1-yl, 2,5-dimethylpyrrol-1-yl; or 2,5-diphenylpyrrol-1-yl;
or substituted or unsubstituted indol-1-yl;
$R^5$=C$_{6-20}$ aryl or C$_{4-10}$ alkyl; optionally substituted.
$R^z$=neutral ligand;
n=0 or 1;
or
a compound of formula (II):

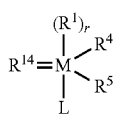
(II)

wherein
M=Ru;
each of $R^1$ and L is a neutral ligand;
r=1-3;
each of $R^4$ and $R^5$ is independently bonded to M through sulfur or oxygen; or $R^4$ and $R^5$ are halogen;

$R^{14}$ is a carbene;
or
a compound of formula (III):

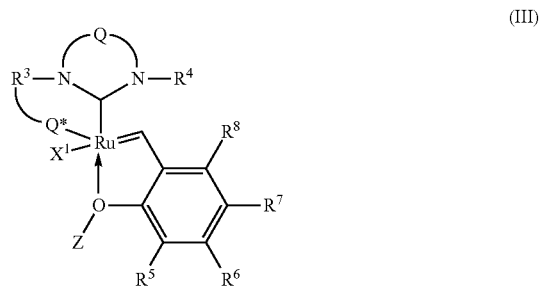
(III)

wherein
Q is a hydrocarbylene, or alkyl-substituted hydrocarbylene;
Q* forms a carbon-ruthenium bond with the carbon from the $R^3$ group;
$X^1$ is nitrate, or C$_{1-20}$ alkylcarboxylate;
$R^3$ is cycloalkyl or an alkyl substituted cycloalkyl group;
$R^4$ is an alkyl substituted aryl group;
Z is alkyl; and
$R^5$, $R^6$, $R^7$ and $R^8$ are hydrogen.

2. The method of claim 1, wherein said third olefin is ethylene.

3. The method of claim 1, wherein the ratio of the E-isomer to the Z-isomer is in the range of from 2:1 to 9:1.

4. The method of claim 1, wherein step (B3) comprises reacting the diol obtained in step (B2) with thiophosgen or 1,1'-thiocarbonyldiimidazol; and step (B4) comprises reacting the 1,3-dioxolane with a trialkylphosphite; or
wherein step (B3) comprises reacting the diol or beta-hydroxy ether obtained in step (B2) with an ortho ester; and step (B4) comprises pyrolysis of the formed 1,3-dioxolane.

5. The method of claim 1, wherein the first olefin used in step (A) comprises a mixture of an E-9-dodecenoate and a Z-9-dodecenoate, the olefin contained in the reaction mixture obtained in step (A) is the E-9-dodecenoate, and the second olefin obtained after step (B) is the Z-9-dodecenoate.

6. The method of claim 1, wherein the ratio of the Z-isomer to the E-isomer is at least 9:1.

7. The method of claim 1, wherein said second olefin is said E-isomer, and step (A) comprises step (A11):
(A11) subjecting the first olefin to a cross metathesis reaction with a fourth olefin in the presence of the metal complex to form a fifth olefin, wherein the metal complex is configured to favour the formation of the Z-isomer over the formation of the E-isomer of the fifth olefin.

8. The method of claim 7, further comprising the subsequent conversion of the Z-isomer into the E-isomer to form the second olefin, wherein step (B) comprises steps (B11) to (B14):
(B11) epoxidizing said Z-isomer to form the epoxide;
(B12) subjecting the epoxide obtained in step (B11) to hydrolysis to form a diol or to alcoholysis to form a beta-hydroxy ether;
(B13) converting the diol or beta-hydroxy ether obtained in step (B12) to a 1,3-dioxolane; and
(B14) degrading the 1,3-dioxolane obtained in step (B13) to form the second olefin in the form of its E-isomer.

9. The method of claim 1,
wherein the first olefin comprises an E-isomer and a Z-isomer of the olefin; and wherein the ratio of the Z-isomer to the E-isomer is at least 9:1; wherein said second olefin is said E-isomer, and step (A) comprises step (A11):

(A11) subjecting the first olefin to a cross metathesis reaction with a fourth olefin in the presence of the metal complex to form a fifth olefin, wherein the metal complex is configured to favour the formation of the Z-isomer over the formation of the E-isomer of the fifth olefin;

and further comprising the subsequent conversion of the Z-isomer into the E-isomer to form the second olefin, wherein step (B) comprises steps (B11) to (B14):

(B11) epoxidizing said Z-isomer to form the expoxide;

(B12) subjecting the epoxide obtained in step (B11) to hydrolysis to form a diol or to alcoholysis to form a beta-hydroxy ether;

(B13) converting the diol or beta-hydroxy ether obtained in step (B12) to a 1,3-dioxolane; and (B14) degrading the 1,3-dioxolane obtained in step (B13) to form the second olefin in the form of its E-isomer.

10. The method of claim 7, wherein the first and the fourth olefin are identical and are a 9-decenoate.

11. The method of claim 1, wherein the catalyst is selected from

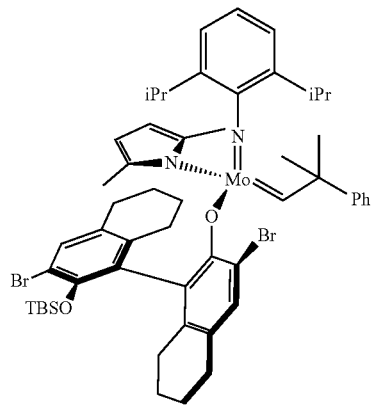

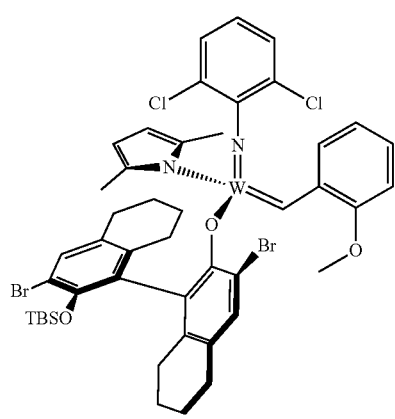

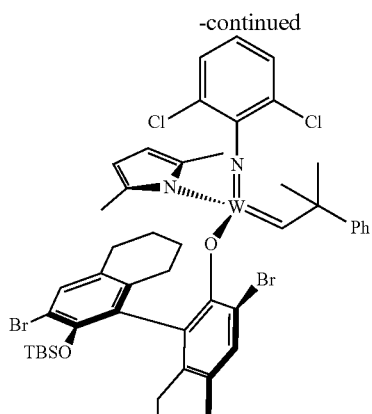

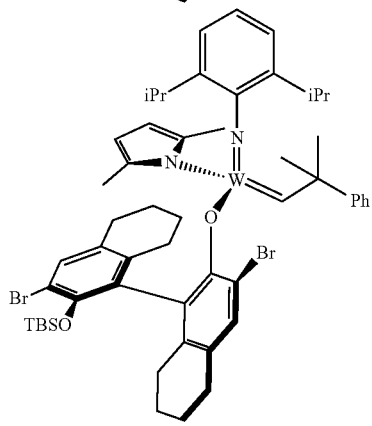

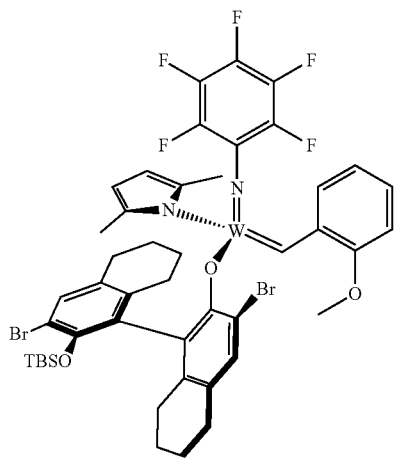

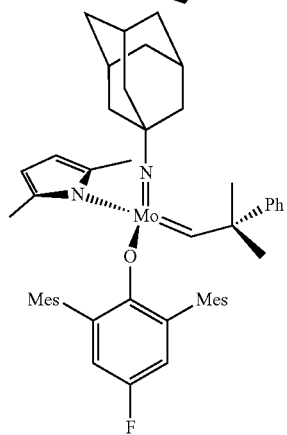

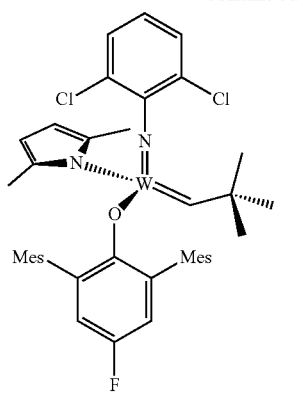
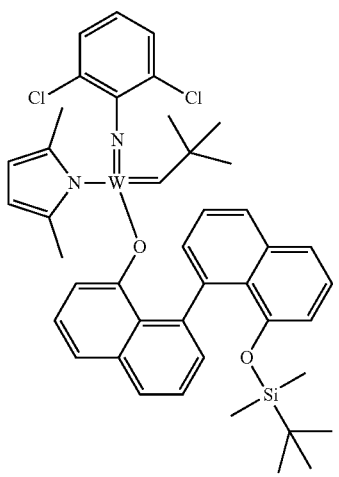
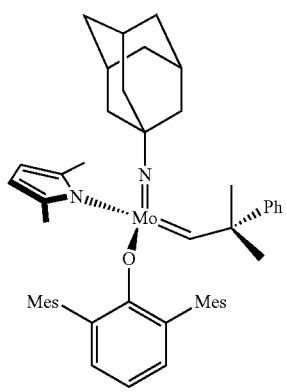
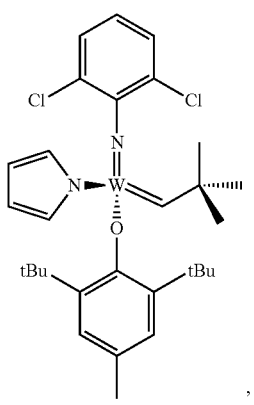
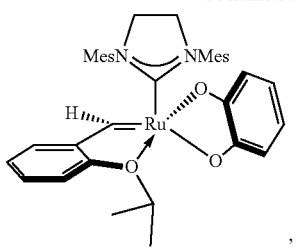
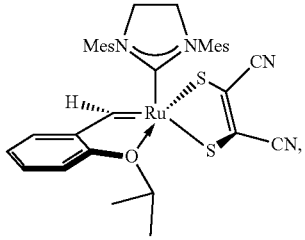
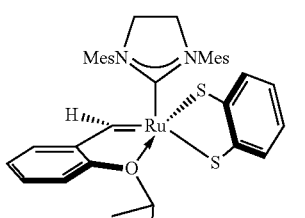
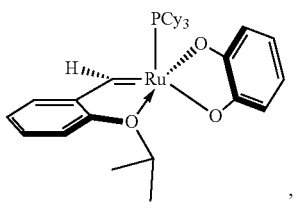
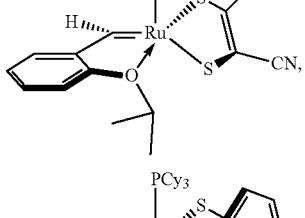
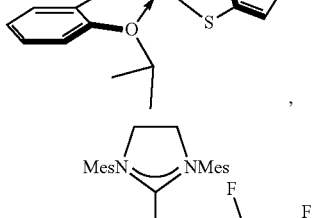
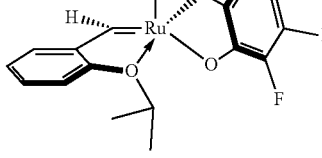

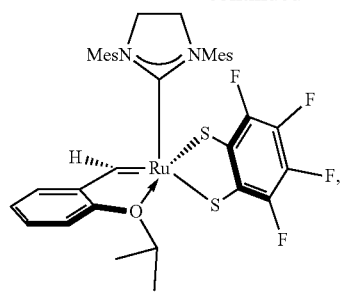
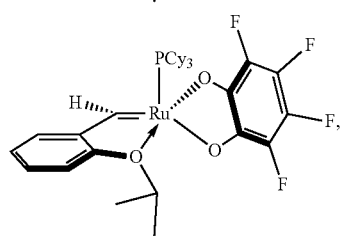
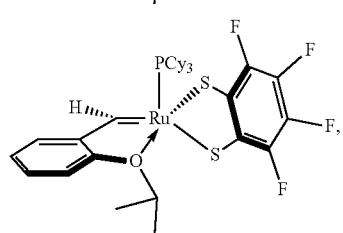
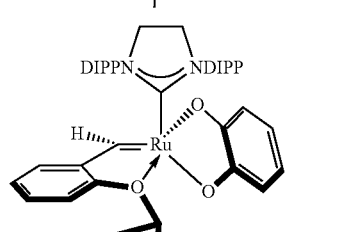
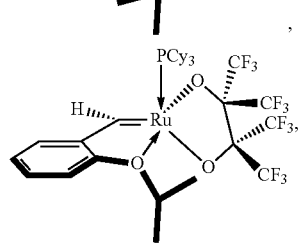
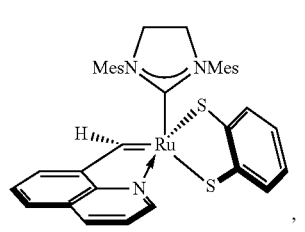
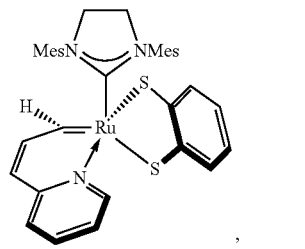
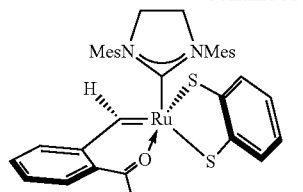
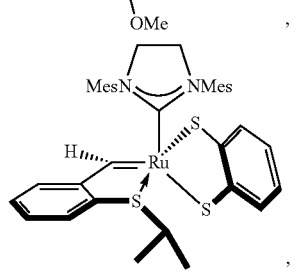
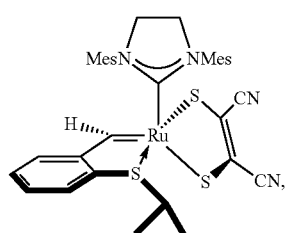
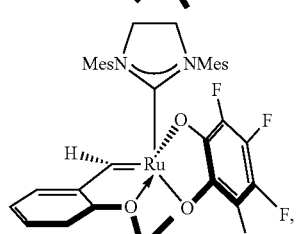
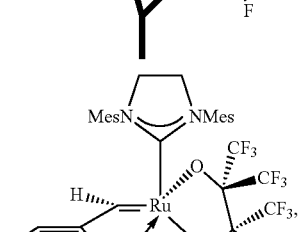
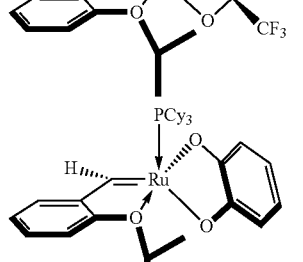
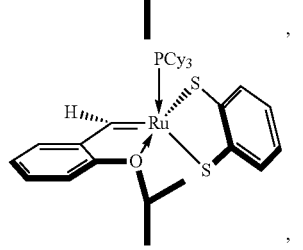

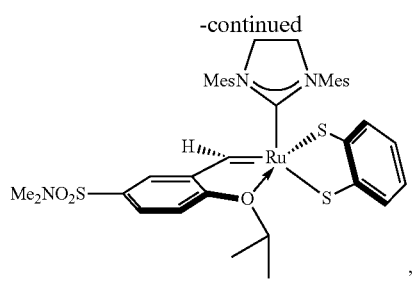
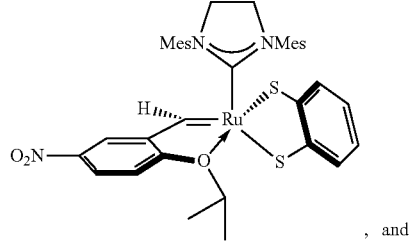
, and
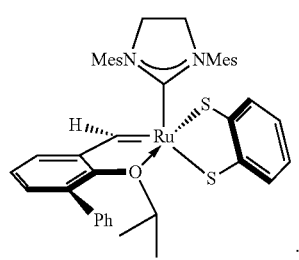
.
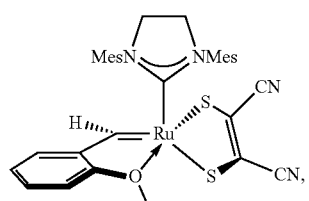
,
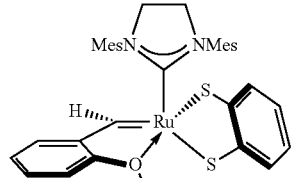
,
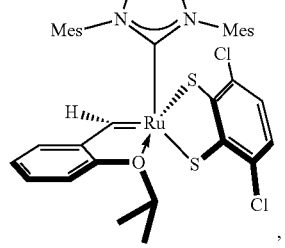
,
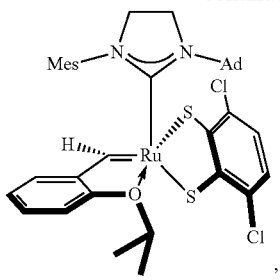
,
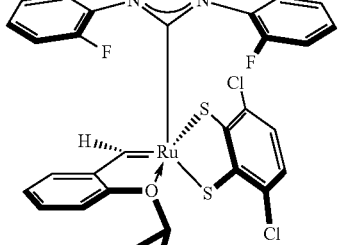
,
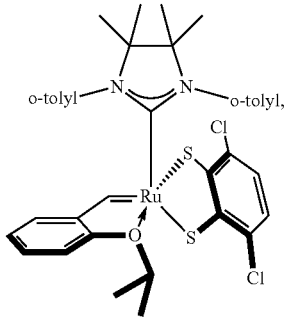
,
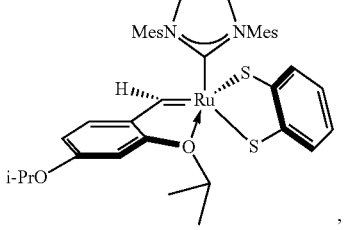
,
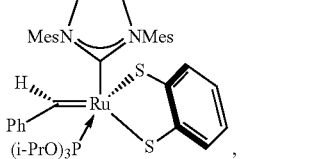
,
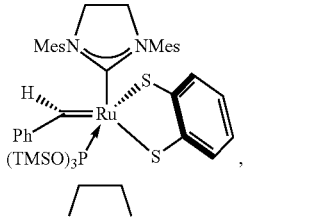
,
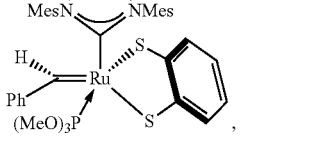
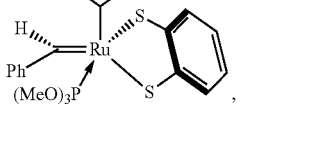
, -continued

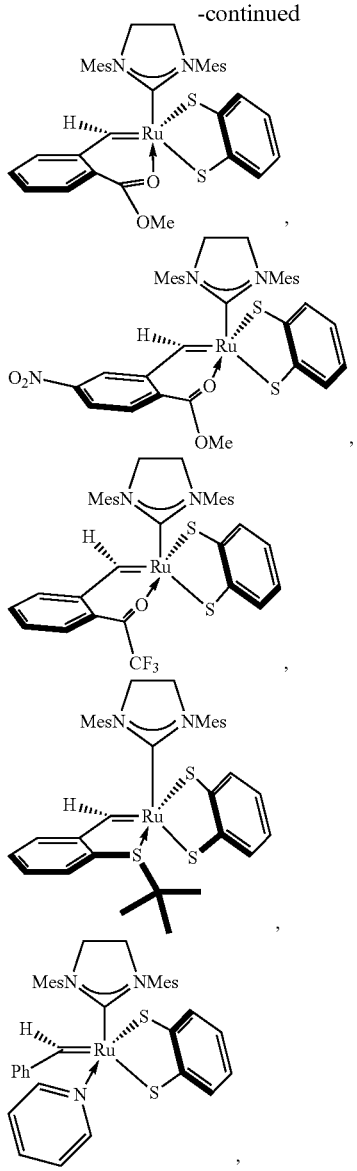

-continued

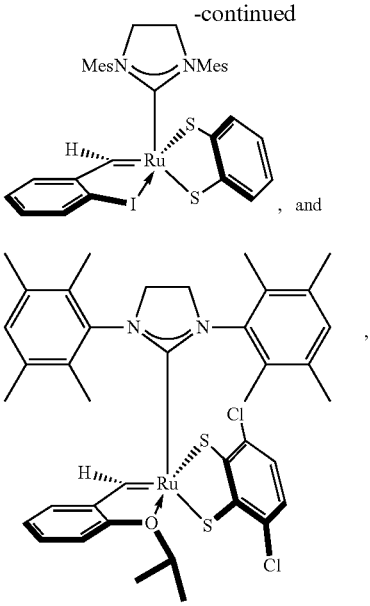

, and (Mes=mesityl; Cy=cyclohexyl; DIPP=diisopropyphenyl; TBS=tent.-butyldimethylsilyl; mes=mesitylene; Ad=1-adamantyl; Ph=phenyl; TMS=trimethylsilyl, Me=methyl; Pr=propyl).

12. The method of claim 1, wherein in compound II, $R^4$ and $R^5$ are Cl.

13. The method of claim 1, wherein said first olefin bears one or more functional groups.

14. The method of claim 1, wherein said one or more functional groups are selected from ester groups, ether groups, amido groups, halogen groups and protected hydroxyl groups, protected carboxylic groups and protected aldehyde groups.

15. The method of claim 1, wherein in compound I, $R^3$ is substituted phenyloxy, substituted naphthyl-2-oxy or substituted 5,6,7,8-tetrahydronaphthyl-2-oxy, or substituted naphthyl-1-oxy.

* * * * *